US012409050B2

(12) United States Patent
Logan et al.

(10) Patent No.: US 12,409,050 B2
(45) Date of Patent: *Sep. 9, 2025

(54) BONE FUSION DEVICE, APPARATUS AND METHOD

(71) Applicant: Neuropro Technologies, Inc., Modesto, CA (US)

(72) Inventors: Joseph N. Logan, Trumbull, CT (US); Gary R. McLuen, Port Townsend, WA (US); Daniel R. Baker, Seattle, WA (US)

(73) Assignee: Neuropro Technologies, Inc., Modesto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/641,692

(22) Filed: Apr. 22, 2024

(65) Prior Publication Data

US 2024/0268974 A1 Aug. 15, 2024

Related U.S. Application Data

(60) Continuation of application No. 17/872,305, filed on Jul. 25, 2022, now Pat. No. 11,963,884, which is a
(Continued)

(51) Int. Cl.
*A61F 2/44* (2006.01)
*A61F 2/30* (2006.01)

(52) U.S. Cl.
CPC .... *A61F 2/447* (2013.01); *A61F 2002/30266* (2013.01); *A61F 2002/304* (2013.01);
(Continued)

(58) Field of Classification Search
CPC ...... A61F 2/4455; A61F 2/446; A61F 2/4465; A61F 2/447
See application file for complete search history.

(56) References Cited

U.S. PATENT DOCUMENTS

| 4,309,777 A | 1/1982 | Patil |
| 4,388,921 A | 6/1983 | Sutter |

(Continued)

FOREIGN PATENT DOCUMENTS

| CN | 1777352 A | 5/2006 |
| CN | 201194047 | 2/2009 |

(Continued)

OTHER PUBLICATIONS

Australian Examination Report No. 1 dated Nov. 8, 2017, from Australian Patent Application No. 2014236698.
(Continued)

*Primary Examiner* — Si Ming Ku
(74) *Attorney, Agent, or Firm* — Haverstock & Owens, A Law Corporation

(57) ABSTRACT

A bodiless bone fusion method, apparatus and device for insertion between bones that are to be fused together and/or in place of one or more of the bones, such as, for example, the vertebrae of a spinal column. The bodiless bone fusion device comprises one or more extendable plates, one or more extending blocks in communication with the extendable plates, one or more positioning elements for adjusting the extendable plates by manipulating the extending blocks, and one or more support panels for holding the positioning elements and guiding the extendable plates. The plates are able to be advantageously positioned in the confined space between the vertebrae to help brace the device until the bone has fused.

20 Claims, 10 Drawing Sheets

Related U.S. Application Data continuation of application No. 16/789,128, filed on Feb. 12, 2020, now Pat. No. 11,399,956, which is a continuation of application No. 16/119,809, filed on Aug. 31, 2018, now Pat. No. 10,575,966, which is a division of application No. 14/210,094, filed on Mar. 13, 2014, now Pat. No. 10,098,757.

(60) Provisional application No. 61/858,505, filed on Jul. 25, 2013, provisional application No. 61/794,789, filed on Mar. 15, 2013.

(52) U.S. Cl.
CPC .............. *A61F 2002/30401* (2013.01); *A61F 2002/30411* (2013.01); *A61F 2002/305* (2013.01); *A61F 2002/30505* (2013.01); *A61F 2002/30556* (2013.01); *A61F 2002/30563* (2013.01); *A61F 2002/30565* (2013.01); *A61F 2002/30579* (2013.01); *A61F 2002/30785* (2013.01); *A61F 2002/30825* (2013.01); *A61F 2002/30904* (2013.01)

(56) References Cited

U.S. PATENT DOCUMENTS

| | | |
|---|---|---|
| 4,863,476 A | 9/1989 | Sheppard |
| 4,961,740 A | 10/1990 | Ray et al. |
| 5,015,247 A | 5/1991 | Michelson |
| 5,059,193 A | 10/1991 | Kuslich |
| 5,123,926 A | 6/1992 | Pisharodi |
| 5,171,278 A | 12/1992 | Pisharodi |
| 5,443,514 A | 8/1995 | Steffee |
| 5,458,642 A | 10/1995 | Beer et al. |
| 5,489,307 A | 2/1996 | Kuslich et al. |
| 5,522,899 A | 6/1996 | Michelson |
| 5,554,191 A | 9/1996 | Lahille et al. |
| 5,653,763 A | 8/1997 | Allen |
| 5,658,335 A | 8/1997 | Allen |
| 5,665,122 A | 9/1997 | Kambin |
| 5,693,100 A | 12/1997 | Pisharodi |
| 5,702,391 A | 12/1997 | Lin |
| 5,716,415 A | 2/1998 | Steffee |
| 5,782,832 A | 7/1998 | Larsen et al. |
| 5,800,547 A | 9/1998 | Schafer et al. |
| 5,800,550 A | 9/1998 | Sertich |
| 5,827,328 A | 10/1998 | Buttermann |
| 5,865,848 A | 2/1999 | Baker |
| 5,885,287 A | 3/1999 | Bagby |
| 5,928,284 A | 7/1999 | Mehdizadeh |
| 5,980,522 A | 11/1999 | Koros et al. |
| 6,019,765 A | 2/2000 | Thornhill |
| 6,045,579 A | 4/2000 | Hochshuler et al. |
| 6,080,158 A | 6/2000 | Lin |
| 6,080,193 A | 6/2000 | Hochshuler et al. |
| 6,102,949 A | 8/2000 | Biedermann et al. |
| 6,102,950 A | 8/2000 | Vaccaro |
| 6,117,174 A | 9/2000 | Nolan |
| 6,129,763 A | 10/2000 | Chauvin et al. |
| 6,156,067 A | 12/2000 | Bryan et al. |
| 6,159,244 A | 12/2000 | Suddaby |
| 6,174,311 B1 | 1/2001 | Branch |
| 6,174,334 B1 | 1/2001 | Suddaby |
| 6,176,881 B1 | 1/2001 | Schar et al. |
| 6,176,882 B1 | 1/2001 | Biedermann et al. |
| 6,179,873 B1 | 1/2001 | Zientek |
| 6,183,517 B1 | 2/2001 | Suddaby |
| 6,190,414 B1 | 2/2001 | Young et al. |
| 6,231,609 B1 | 5/2001 | Mehdizadeh |
| 6,319,257 B1 | 11/2001 | Carignan et al. |
| 6,342,074 B1 | 1/2002 | Simpson |
| 6,368,351 B1 | 4/2002 | Glenn et al. |
| 6,371,968 B1 | 4/2002 | Kogasaka et al. |
| 6,371,987 B1 | 4/2002 | Weiland et al. |
| 6,375,655 B1 | 4/2002 | Zdeblick et al. |
| 6,375,683 B1 | 4/2002 | Crozet et al. |
| 6,383,190 B1 | 5/2002 | Preissman |
| 6,387,130 B1 | 5/2002 | Stone |
| 6,409,766 B1 | 6/2002 | Brett |
| 6,419,705 B1 | 7/2002 | Erickson |
| 6,436,140 B1 | 8/2002 | Liu et al. |
| 6,443,989 B1 | 9/2002 | Jackson |
| 6,454,806 B1 | 9/2002 | Cohen et al. |
| 6,454,807 B1 | 9/2002 | Jackson |
| 6,464,727 B1 | 10/2002 | Sharkey et al. |
| 6,488,710 B2 | 12/2002 | Besselink |
| 6,491,695 B1 | 12/2002 | Roggenbuck |
| 6,527,803 B1 | 3/2003 | Crozet et al. |
| 6,562,041 B1 | 5/2003 | Yonemura et al. |
| 6,562,074 B2 | 5/2003 | Gerbec |
| 6,572,619 B2 | 6/2003 | Santilli |
| 6,572,653 B1 | 6/2003 | Simonson |
| 6,575,042 B1 | 6/2003 | Rinner |
| 6,576,016 B1 | 6/2003 | Hochshuler et al. |
| 6,582,431 B1 | 6/2003 | Ray |
| 6,582,451 B1 | 6/2003 | Rinner |
| 6,582,467 B1 | 6/2003 | Teitelbaum et al. |
| 6,595,995 B2 | 7/2003 | Zdeblick et al. |
| 6,610,090 B1 | 8/2003 | Bohm |
| 6,613,091 B1 | 9/2003 | Zdeblick et al. |
| 6,616,695 B1 | 9/2003 | Crozet |
| 6,641,614 B1 | 11/2003 | Wagner |
| 6,645,249 B2 | 11/2003 | Ralph et al. |
| 6,652,584 B2 | 11/2003 | Michelson |
| 6,666,888 B1 | 12/2003 | Jackson |
| 6,685,742 B1 | 2/2004 | Jackson |
| 6,706,070 B1 | 3/2004 | Wagner et al. |
| 6,709,458 B2 | 3/2004 | Michelson |
| 6,723,126 B1 | 4/2004 | Berry |
| 6,723,128 B2 | 4/2004 | Uk |
| 6,746,454 B2 | 6/2004 | Winterbottom et al. |
| 6,767,367 B1 | 7/2004 | Michelson |
| 6,770,095 B2 | 8/2004 | Grinberg et al. |
| 6,770,096 B2 | 8/2004 | Bolger et al. |
| 6,808,537 B2 | 10/2004 | Michelson |
| 6,814,756 B1 | 11/2004 | Michelson |
| 6,821,298 B1 | 11/2004 | Jackson |
| 6,830,589 B2 | 12/2004 | Erickson |
| 6,835,206 B2 | 12/2004 | Jackson |
| 6,902,568 B2 | 6/2005 | Serhan |
| 6,923,830 B2 | 8/2005 | Michelson |
| 6,962,606 B2 | 11/2005 | Michelson |
| 6,979,353 B2 | 12/2005 | Bresina |
| 6,989,011 B2 | 1/2006 | Paul et al. |
| 7,008,453 B1 | 3/2006 | Michelson |
| 7,018,415 B1 | 3/2006 | McKay |
| 7,041,309 B2 | 5/2006 | Remington et al. |
| 7,048,763 B2 | 5/2006 | Ralph et al. |
| 7,094,257 B2 | 8/2006 | Mujwid et al. |
| 7,097,648 B1 | 8/2006 | Globerman |
| 7,108,862 B2 | 9/2006 | Remington et al. |
| 7,118,598 B2 | 10/2006 | Michelson |
| 7,128,760 B2 | 10/2006 | Michelson |
| 7,166,130 B2 | 1/2007 | Ferree |
| 7,172,561 B2 | 2/2007 | Grimberg |
| 7,211,112 B2 | 5/2007 | Baynham et al. |
| 7,217,291 B2 | 5/2007 | Zucherman et al. |
| 7,217,293 B2 | 5/2007 | Branch, Jr. |
| 7,220,280 B2 | 5/2007 | Kast et al. |
| 7,235,103 B2 | 6/2007 | Rivin |
| 7,238,186 B2 | 7/2007 | Zdeblick et al. |
| 7,282,063 B2 | 10/2007 | Cohen et al. |
| 7,331,994 B2 | 2/2008 | Gordon et al. |
| 7,331,996 B2 | 2/2008 | Soto et al. |
| 7,362,251 B2 | 4/2008 | Jensen et al. |
| 7,431,735 B2 | 10/2008 | Liu et al. |
| 7,445,636 B2 | 11/2008 | Michelson |
| 7,479,160 B2 | 1/2009 | Branch et al. |
| 7,500,992 B2 | 3/2009 | Li |
| 7,537,612 B2 | 5/2009 | Kunzler |
| 7,578,849 B2 | 8/2009 | Trieu |
| 7,584,682 B2 | 9/2009 | Hsiao |
| 7,588,573 B2 | 9/2009 | Berry |

(56) References Cited

U.S. PATENT DOCUMENTS

| | | |
|---|---|---|
| 7,608,107 B2 | 10/2009 | Michelson |
| 7,621,956 B2 | 11/2009 | Paul et al. |
| 7,637,952 B2 | 12/2009 | Landry |
| 7,674,296 B2 | 3/2010 | Rhonda et al. |
| 7,678,148 B2 | 3/2010 | Peterman |
| 7,682,376 B2 | 3/2010 | Trieu |
| 7,691,147 B2 | 4/2010 | Gutlin et al. |
| 7,703,727 B2 | 4/2010 | Selness |
| 7,727,280 B2 * | 6/2010 | McLuen ............ A61F 2/4455 623/17.16 |
| 7,749,252 B2 | 7/2010 | Zucherman et al. |
| 7,753,958 B2 | 7/2010 | Gordon et al. |
| 7,758,617 B2 | 7/2010 | Lott et al. |
| 7,794,501 B2 | 9/2010 | Edie et al. |
| 7,799,081 B2 | 9/2010 | McKinley |
| D626,233 S | 10/2010 | Cipoletti et al. |
| 7,811,287 B2 | 10/2010 | Errico et al. |
| 7,811,327 B2 | 10/2010 | Hansell et al. |
| 7,828,849 B2 | 11/2010 | Lin |
| 7,837,688 B2 | 11/2010 | Boyer, II et al. |
| 7,837,734 B2 | 11/2010 | Zucherman et al. |
| 7,850,733 B2 | 12/2010 | Baynham et al. |
| 7,931,688 B2 | 4/2011 | Landry et al. |
| 7,932,825 B2 | 4/2011 | Berger |
| 7,935,117 B2 | 5/2011 | Sackett et al. |
| RE42,480 E | 6/2011 | Bryan et al. |
| 7,985,231 B2 | 7/2011 | Sankaran |
| 8,002,834 B2 | 8/2011 | de Villiers et al. |
| 8,011,004 B2 | 8/2011 | Kim et al. |
| 8,043,295 B2 | 10/2011 | Reed |
| 8,062,375 B2 | 11/2011 | Glerum et al. |
| 8,070,813 B2 | 12/2011 | Grotz et al. |
| 8,088,402 B2 | 1/2012 | Remington et al. |
| 8,105,382 B2 | 1/2012 | Olmos et al. |
| 8,114,092 B2 | 2/2012 | Altarac |
| 8,187,331 B2 | 5/2012 | Strohkirch, Jr |
| 8,187,332 B2 | 5/2012 | McLuen |
| 8,221,502 B2 | 7/2012 | Branch, Jr. |
| 8,262,666 B2 | 9/2012 | Baynham et al. |
| 8,262,736 B2 | 9/2012 | Michelson |
| 8,267,968 B2 | 9/2012 | Remington et al. |
| 8,273,129 B2 | 9/2012 | Baynham et al. |
| 8,282,683 B2 | 10/2012 | Mclaughlin et al. |
| 8,292,963 B2 | 10/2012 | Miller et al. |
| 8,303,601 B2 | 11/2012 | Bandeira et al. |
| 8,303,658 B2 | 11/2012 | Peterman |
| 8,308,801 B2 | 11/2012 | Halverson et al. |
| 8,308,804 B2 | 11/2012 | Kreuger et al. |
| 8,308,805 B2 | 11/2012 | Lynn |
| 8,317,025 B1 | 11/2012 | Kolozs et al. |
| 8,317,798 B2 | 11/2012 | Lim |
| 8,328,962 B2 | 12/2012 | Schussler |
| 8,337,562 B2 | 12/2012 | Landry et al. |
| 8,343,222 B2 | 1/2013 | Cope |
| 8,361,152 B2 | 1/2013 | McCormack et al. |
| 8,366,777 B2 | 2/2013 | Matthis et al. |
| 8,403,990 B2 | 3/2013 | Dryer et al. |
| 8,435,298 B2 | 5/2013 | Weiman |
| 8,444,696 B2 | 5/2013 | Michelson |
| 8,444,697 B1 | 5/2013 | Butler et al. |
| 8,454,623 B2 | 6/2013 | Patel |
| 8,485,075 B1 | 7/2013 | Gauthier et al. |
| 8,579,904 B2 | 11/2013 | Siccardi |
| 8,585,763 B2 | 11/2013 | Olevsky et al. |
| 8,591,587 B2 | 11/2013 | Refai et al. |
| 8,597,360 B2 | 12/2013 | McLuen et al. |
| 8,690,886 B2 | 4/2014 | Li |
| 8,734,337 B2 | 5/2014 | Deitch |
| 8,740,980 B2 | 6/2014 | Merves |
| 8,894,710 B2 | 11/2014 | Simpson et al. |
| 8,932,355 B2 | 1/2015 | Grotz |
| 8,940,049 B1 | 1/2015 | Jimenez |
| 9,119,725 B2 | 9/2015 | Barrall |
| 9,155,629 B2 | 10/2015 | Remington et al. |
| 9,186,262 B2 | 11/2015 | McLuen et al. |
| 9,216,098 B2 | 12/2015 | Trudeau |
| 9,301,853 B2 | 4/2016 | Richter |
| 9,308,098 B2 | 4/2016 | Boehn |
| 9,320,610 B2 | 4/2016 | Alheidt et al. |
| 9,351,848 B2 | 5/2016 | Glerum |
| 9,358,123 B2 | 6/2016 | McLuen et al. |
| 9,358,672 B2 | 6/2016 | Gautheir et al. |
| 9,445,920 B2 | 9/2016 | Baynham |
| 9,492,283 B2 | 11/2016 | Glerum |
| 9,526,525 B2 | 12/2016 | Remington et al. |
| 9,532,883 B2 | 1/2017 | McLuen et al. |
| 9,545,283 B2 | 1/2017 | Sack |
| 9,655,740 B1 | 5/2017 | Faulkner |
| 9,700,425 B1 | 7/2017 | Smith |
| 9,724,208 B2 | 8/2017 | Robinson |
| 9,737,316 B2 | 8/2017 | Bertagnoli |
| 9,750,617 B2 | 9/2017 | Lim |
| 9,750,618 B1 | 9/2017 | Daffison |
| 9,757,111 B2 | 9/2017 | Fehling |
| 9,757,249 B2 | 9/2017 | Radcliffe |
| 9,757,250 B2 | 9/2017 | Josse |
| 9,782,267 B2 | 10/2017 | Barrall |
| 9,782,271 B2 | 10/2017 | Cipoletti |
| 9,801,734 B1 | 10/2017 | Stein |
| 9,872,779 B2 | 1/2018 | Miller |
| 9,913,224 B2 | 3/2018 | Lou et al. |
| 9,949,841 B2 | 4/2018 | Glerum |
| 9,974,665 B2 | 5/2018 | McLuen et al. |
| 10,016,283 B2 | 7/2018 | McLuen et al. |
| 10,052,215 B2 | 8/2018 | Hessler |
| 10,092,422 B2 | 10/2018 | McLuen et al. |
| 10,098,757 B2 | 10/2018 | Logan et al. |
| 10,111,760 B2 | 10/2018 | Knapp et al. |
| 10,159,583 B2 | 12/2018 | Dietzel et al. |
| 10,172,718 B2 | 1/2019 | Wolters |
| 10,213,321 B2 | 2/2019 | Knapp et al. |
| 10,292,830 B2 | 5/2019 | McLuen et al. |
| 10,398,563 B2 | 9/2019 | Engstrom |
| 10,420,654 B2 | 9/2019 | Logan et al. |
| 10,470,891 B2 | 11/2019 | Sharifi-Mehr |
| 10,575,966 B2 | 3/2020 | Logan et al. |
| 10,682,240 B2 | 6/2020 | McLuen |
| 10,709,574 B2 | 7/2020 | McLuen |
| 10,729,560 B2 | 8/2020 | Baker et al. |
| 10,729,562 B2 | 8/2020 | Knapp et al. |
| 10,736,754 B2 | 8/2020 | McLuen |
| 10,973,657 B2 | 4/2021 | Remington et al. |
| 11,141,289 B2 | 10/2021 | Knapp et al. |
| 11,399,956 B2 | 8/2022 | Logan et al. |
| 11,432,940 B2 | 9/2022 | Logan et al. |
| 11,439,517 B2 | 9/2022 | McLuen et al. |
| 11,452,616 B2 | 9/2022 | McLuen et al. |
| 11,458,029 B2 | 10/2022 | Knapp et al. |
| 11,497,623 B2 | 11/2022 | Baker et al. |
| 11,583,414 B2 | 2/2023 | McLuen |
| 11,963,884 B2 | 4/2024 | Logan et al. |
| 2001/0021852 A1 | 9/2001 | Chappius |
| 2002/0033305 A1 | 3/2002 | Koyama et al. |
| 2002/0049445 A1 | 4/2002 | Hall, IV |
| 2002/0128713 A1 | 9/2002 | Ferree |
| 2002/0128716 A1 | 9/2002 | Cohen et al. |
| 2002/0165613 A1 | 11/2002 | Lin et al. |
| 2003/0036762 A1 | 2/2003 | Kerr |
| 2003/0109932 A1 | 6/2003 | Keynan |
| 2003/0149484 A1 | 8/2003 | Michelson |
| 2003/0229355 A1 | 12/2003 | Keller |
| 2003/0232065 A1 | 12/2003 | Remington et al. |
| 2003/0236520 A1 | 12/2003 | Lim |
| 2004/0024461 A1 | 2/2004 | Ferree |
| 2004/0039448 A1 | 2/2004 | Pisharodi |
| 2004/0068269 A1 | 4/2004 | Bonati |
| 2004/0087947 A1 | 5/2004 | Lim et al. |
| 2004/0087949 A1 | 5/2004 | Lim et al. |
| 2004/0102077 A1 | 5/2004 | Trieu |
| 2004/0102774 A1 | 5/2004 | Trieu |
| 2004/0106998 A1 | 6/2004 | Ferree |
| 2004/0127993 A1 | 7/2004 | Kast et al. |
| 2004/0138750 A1 | 7/2004 | Michell |
| 2004/0148027 A1 | 7/2004 | Errico et al. |

(56) References Cited

U.S. PATENT DOCUMENTS

| | | |
|---|---|---|
| 2004/0153065 A1 | 8/2004 | Lim |
| 2004/0181285 A1 | 9/2004 | Simonson |
| 2004/0204715 A1 | 10/2004 | Evans |
| 2004/0204762 A1 | 10/2004 | Ralph et al. |
| 2004/0225292 A1 | 11/2004 | Sasso |
| 2004/0230309 A1 | 11/2004 | DiMauro et al. |
| 2004/0243238 A1 | 12/2004 | Arnin et al. |
| 2004/0254643 A1 | 12/2004 | Jackson |
| 2005/0015149 A1 | 1/2005 | Michelson |
| 2005/0021042 A1 | 1/2005 | Marnay |
| 2005/0027360 A1 | 2/2005 | Webb et al. |
| 2005/0033432 A1 | 2/2005 | Gordon |
| 2005/0038515 A1 | 2/2005 | Kunzler |
| 2005/0065610 A1 | 3/2005 | Pisharodi |
| 2005/0107877 A1 | 5/2005 | Blain |
| 2005/0107878 A1 | 5/2005 | Conchy |
| 2005/0182416 A1 | 8/2005 | Lim et al. |
| 2005/0278036 A1 | 12/2005 | Leonard et al. |
| 2005/0283236 A1 | 12/2005 | Razin |
| 2006/0052872 A1 | 3/2006 | Studer et al. |
| 2006/0058807 A1 | 3/2006 | Landry |
| 2006/0058880 A1 | 3/2006 | Wysocki |
| 2006/0069436 A1 | 3/2006 | Sutton et al. |
| 2006/0074431 A1 | 4/2006 | Sutton |
| 2006/0095136 A1 | 5/2006 | McLuen |
| 2006/0116769 A1 | 6/2006 | Marnay et al. |
| 2006/0122701 A1 | 6/2006 | Keister |
| 2006/0129244 A1 | 6/2006 | Ensign |
| 2006/0142859 A1 | 6/2006 | McLuen |
| 2006/0149381 A1 | 7/2006 | Kim |
| 2006/0155295 A1 | 7/2006 | Supper |
| 2006/0190084 A1 | 8/2006 | Doubler et al. |
| 2006/0200243 A1 | 9/2006 | Rothman et al. |
| 2006/0200244 A1 | 9/2006 | Assaker |
| 2006/0233853 A1 | 10/2006 | Remington et al. |
| 2006/0235426 A1 | 10/2006 | Lim |
| 2006/0241643 A1 | 10/2006 | Lim et al. |
| 2006/0241764 A1 | 10/2006 | Michelson |
| 2006/0241766 A1 | 10/2006 | Felton et al. |
| 2006/0241767 A1 | 10/2006 | Doty |
| 2006/0241770 A1 | 10/2006 | Rhoda et al. |
| 2006/0241774 A1 | 10/2006 | Attali et al. |
| 2006/0247679 A1 | 11/2006 | Peterman |
| 2006/0253201 A1 | 11/2006 | McLuen |
| 2006/0276899 A1 | 12/2006 | Zipnick et al. |
| 2006/0293752 A1 | 12/2006 | Mourmene et al. |
| 2006/0293753 A1 | 12/2006 | Thramann |
| 2007/0049943 A1 | 3/2007 | Moskowitz |
| 2007/0050030 A1 | 3/2007 | Kim |
| 2007/0067038 A1 | 3/2007 | Studer et al. |
| 2007/0093897 A1 | 4/2007 | Gerbee et al. |
| 2007/0093901 A1 | 4/2007 | Grotz et al. |
| 2007/0179610 A1 | 8/2007 | Biedermann |
| 2007/0191954 A1 | 8/2007 | Hansell et al. |
| 2007/0209222 A1 | 9/2007 | Fischer |
| 2007/0213641 A1 | 9/2007 | Francis |
| 2007/0233254 A1 | 10/2007 | Grotz et al. |
| 2007/0255407 A1 | 11/2007 | Castleman et al. |
| 2007/0255409 A1 | 11/2007 | Dickson |
| 2007/0255413 A1 | 11/2007 | Edie et al. |
| 2007/0255415 A1 | 11/2007 | Edie et al. |
| 2007/0260260 A1 | 11/2007 | Hanh |
| 2007/0270954 A1 | 11/2007 | Wu |
| 2007/0270964 A1 | 11/2007 | Strohkirch |
| 2007/0270968 A1 | 11/2007 | Baynham et al. |
| 2007/0282372 A1 | 12/2007 | Yedlicka |
| 2007/0282441 A1 | 12/2007 | Stream et al. |
| 2008/0009868 A1 | 1/2008 | Gotfried et al. |
| 2008/0009880 A1 | 1/2008 | Warnick et al. |
| 2008/0015701 A1 | 1/2008 | Garcia et al. |
| 2008/0021476 A1 | 1/2008 | Kirschman |
| 2008/0021555 A1 | 1/2008 | Gauthier |
| 2008/0021558 A1 | 1/2008 | Thramann |
| 2008/0021559 A1 | 1/2008 | Thramann |
| 2008/0046083 A1 | 2/2008 | Hewko |
| 2008/0051787 A1 | 2/2008 | Remington et al. |
| 2008/0051902 A1 | 2/2008 | Dwyer |
| 2008/0058930 A1 | 3/2008 | Edie |
| 2008/0077153 A1 | 3/2008 | Pernsteiner et al. |
| 2008/0097435 A1 | 4/2008 | Deridder et al. |
| 2008/0114367 A1 | 5/2008 | Gauthier |
| 2008/0125778 A1 | 5/2008 | Li |
| 2008/0132949 A1 | 6/2008 | Aferzon et al. |
| 2008/0140207 A1 | 6/2008 | Olmos et al. |
| 2008/0147193 A1 | 6/2008 | Matthis et al. |
| 2008/0154381 A1 | 6/2008 | Parrish |
| 2008/0161817 A1 | 7/2008 | Parsons et al. |
| 2008/0177275 A1 | 7/2008 | Wing et al. |
| 2008/0208264 A1 | 8/2008 | Lazarof |
| 2008/0269756 A1 | 10/2008 | Tomko |
| 2008/0269905 A1 | 10/2008 | Link |
| 2008/0287995 A1 | 11/2008 | Gauthier |
| 2008/0288073 A1 | 11/2008 | Renganath |
| 2008/0288076 A1 | 11/2008 | Soo et al. |
| 2008/0306489 A1 | 12/2008 | Altarac et al. |
| 2009/0030422 A1 | 1/2009 | Parsons et al. |
| 2009/0099601 A1 | 4/2009 | Aferzon et al. |
| 2009/0105828 A1 | 4/2009 | Gimbel |
| 2009/0112217 A1 | 4/2009 | Hester |
| 2009/0112220 A1 | 4/2009 | Kraus |
| 2009/0112324 A1 | 4/2009 | Refai |
| 2009/0112325 A1 | 4/2009 | Refai |
| 2009/0164017 A1 | 6/2009 | Sommerich |
| 2009/0164018 A1 | 6/2009 | Sommerich |
| 2009/0164020 A1 | 6/2009 | Janowski et al. |
| 2009/0182343 A1 | 7/2009 | Trudeau et al. |
| 2009/0192611 A1 | 7/2009 | Linder |
| 2009/0198241 A1 | 8/2009 | Phan |
| 2009/0198245 A1 | 8/2009 | Phan |
| 2009/0198338 A1 | 8/2009 | Phan |
| 2009/0210061 A1 | 8/2009 | Sledge |
| 2009/0222100 A1 | 9/2009 | Cipoletti et al. |
| 2009/0222101 A1 | 9/2009 | de Villiers et al. |
| 2009/0228110 A1 | 9/2009 | McClintock |
| 2009/0234364 A1 | 9/2009 | Crook |
| 2009/0265008 A1 | 10/2009 | Thibodeau |
| 2009/0292361 A1 | 11/2009 | Lopez |
| 2009/0299478 A1 | 12/2009 | Carls et al. |
| 2009/0306672 A1 | 12/2009 | Reindel et al. |
| 2010/0010494 A1 | 1/2010 | Quimo |
| 2010/0015747 A1 | 1/2010 | Kwon et al. |
| 2010/0023057 A1 | 1/2010 | Aeschlimann et al. |
| 2010/0024487 A1 | 2/2010 | Khoo et al. |
| 2010/0057204 A1 | 3/2010 | Kadaba et al. |
| 2010/0094425 A1 | 4/2010 | Bentley |
| 2010/0100100 A1 | 4/2010 | Refai |
| 2010/0114106 A1 | 5/2010 | Weber |
| 2010/0114183 A1 | 5/2010 | Wassinger et al. |
| 2010/0125334 A1 | 5/2010 | Krueger |
| 2010/0145456 A1 | 6/2010 | Simpson et al. |
| 2010/0168862 A1 | 7/2010 | Edie |
| 2010/0179657 A1 | 7/2010 | Greenhalgh |
| 2010/0204795 A1 | 8/2010 | Greenhalgh |
| 2010/0211119 A1 | 8/2010 | Refai et al. |
| 2010/0211176 A1 | 8/2010 | Greenhalgh |
| 2010/0217404 A1 | 8/2010 | Kane |
| 2010/0222884 A1 | 9/2010 | Greenhalgh |
| 2010/0241231 A1 | 9/2010 | Attia et al. |
| 2010/0256768 A1 | 10/2010 | Lim et al. |
| 2010/0262247 A1 | 10/2010 | Arnin |
| 2010/0274357 A1 | 10/2010 | Miller |
| 2010/0280622 A1 | 11/2010 | McKinley |
| 2010/0286779 A1 | 11/2010 | Thibodeau |
| 2010/0286780 A1 | 11/2010 | Dryer et al. |
| 2010/0292796 A1 | 11/2010 | Greenhalgh et al. |
| 2010/0298939 A1 | 11/2010 | Delfosse et al. |
| 2010/0324606 A1 | 12/2010 | Moskowitz et al. |
| 2010/0331885 A1 | 12/2010 | Remington et al. |
| 2011/0015638 A1 | 1/2011 | Pischi et al. |
| 2011/0015682 A1 | 1/2011 | Lewis |
| 2011/0015741 A1 | 1/2011 | Melkent |
| 2011/0015742 A1 | 1/2011 | Hong |
| 2011/0015747 A1* | 1/2011 | McManus ............ A61F 2/44 623/17.16 |

(56) References Cited

U.S. PATENT DOCUMENTS

| | | |
|---|---|---|
| 2011/0035007 A1 | 2/2011 | Patel |
| 2011/0054621 A1 | 3/2011 | Lim |
| 2011/0077738 A1 | 3/2011 | Ciupik et al. |
| 2011/0087329 A1 | 4/2011 | Poulos |
| 2011/0093074 A1 | 4/2011 | Glerum |
| 2011/0098628 A1 | 4/2011 | Yeung |
| 2011/0112587 A1 | 5/2011 | Patel et al. |
| 2011/0130835 A1 | 6/2011 | Ashley et al. |
| 2011/0130838 A1 | 6/2011 | Lopez |
| 2011/0138948 A1 | 6/2011 | Jimenez et al. |
| 2011/0160861 A1 | 6/2011 | Jimenez et al. |
| 2011/0172716 A1 | 7/2011 | Glerum |
| 2011/0172774 A1 | 7/2011 | Varela |
| 2011/0172779 A1 | 7/2011 | Dickson |
| 2011/0190888 A1 | 8/2011 | Bertele |
| 2011/0202135 A1 | 8/2011 | Baek |
| 2011/0213465 A1 | 9/2011 | Landry et al. |
| 2011/0218627 A1 | 9/2011 | Rampersaud et al. |
| 2011/0230970 A1 | 9/2011 | Lynn et al. |
| 2011/0238184 A1 | 9/2011 | Zdeblick et al. |
| 2011/0251691 A1 | 10/2011 | McLaughlin |
| 2011/0251692 A1 | 10/2011 | McLaughlin |
| 2011/0257751 A1 | 10/2011 | Sherman |
| 2011/0282453 A1 | 11/2011 | Greenhalgh et al. |
| 2011/0301712 A1 | 12/2011 | Palmatier et al. |
| 2011/0307066 A1 | 12/2011 | Lim et al. |
| 2011/0319997 A1 | 12/2011 | Glerum et al. |
| 2012/0035729 A1 | 2/2012 | Glerum et al. |
| 2012/0058451 A1 | 3/2012 | Lazarof |
| 2012/0059470 A1 | 3/2012 | Weiman |
| 2012/0059472 A1 | 3/2012 | Weiman |
| 2012/0059473 A1 | 3/2012 | Weiman |
| 2012/0059474 A1 | 3/2012 | Weiman |
| 2012/0059475 A1 | 3/2012 | Weiman |
| 2012/0059481 A1 | 3/2012 | Abernathie et al. |
| 2012/0064487 A1 | 3/2012 | Lazarof |
| 2012/0064488 A1 | 3/2012 | Lazarof |
| 2012/0071979 A1 | 3/2012 | Zipnick |
| 2012/0089228 A1 | 4/2012 | Poulos |
| 2012/0130493 A1 | 5/2012 | McLaughlin |
| 2012/0130494 A1 | 5/2012 | DeLurio et al. |
| 2012/0136399 A1 | 5/2012 | Seifert |
| 2012/0136448 A1 | 5/2012 | Seifert et al. |
| 2012/0143194 A1 | 6/2012 | Seifert et al. |
| 2012/0143201 A1 | 6/2012 | Seifert et al. |
| 2012/0150304 A1 | 6/2012 | Glerum et al. |
| 2012/0150305 A1 | 6/2012 | Glerum et al. |
| 2012/0158071 A1 | 6/2012 | Jimenez et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0191194 A1 | 7/2012 | Olmos et al. |
| 2012/0197403 A1 | 8/2012 | Merves |
| 2012/0197404 A1 | 8/2012 | Brun et al. |
| 2012/0203347 A1 | 8/2012 | Glerum et al. |
| 2012/0209384 A1 | 8/2012 | Arnold et al. |
| 2012/0209386 A1 | 8/2012 | Triplett |
| 2012/0226357 A1 | 9/2012 | Varela |
| 2012/0232552 A1 | 9/2012 | Lopez |
| 2012/0232601 A1 | 9/2012 | Chabansky et al. |
| 2012/0232659 A1 | 9/2012 | Himmelberger |
| 2012/0232660 A1 | 9/2012 | Davenport |
| 2012/0245691 A1 | 9/2012 | Reimels |
| 2012/0253412 A1 | 10/2012 | Lee |
| 2012/0265303 A1 | 10/2012 | Refai |
| 2012/0271422 A1 | 10/2012 | Miller et al. |
| 2012/0276204 A1 | 11/2012 | Remington et al. |
| 2012/0277810 A1 | 11/2012 | Siccardi et al. |
| 2012/0277875 A1 | 11/2012 | Arnin |
| 2012/0290090 A1 | 11/2012 | Glerum et al. |
| 2012/0300124 A1 | 11/2012 | Yamashita |
| 2012/0303124 A1 | 11/2012 | McLuen et al. |
| 2012/0310350 A1 | 12/2012 | Farris et al. |
| 2012/0323327 A1 | 12/2012 | McAfee |
| 2012/0323328 A1 | 12/2012 | Weiman |
| 2012/0330421 A1 | 12/2012 | Weiman |
| 2012/0330422 A1 | 12/2012 | Weiman |
| 2013/0006358 A1 | 1/2013 | Olevsky |
| 2013/0006359 A1 | 1/2013 | Fedorov |
| 2013/0006361 A1 | 1/2013 | Glerum et al. |
| 2013/0006364 A1 | 1/2013 | McCormack et al. |
| 2013/0018468 A1 | 1/2013 | Moskowitz et al. |
| 2013/0018469 A1 | 1/2013 | Moskowitz et al. |
| 2013/0018470 A1 | 1/2013 | Moskowitz et al. |
| 2013/0023991 A1 | 1/2013 | Moskowitz et al. |
| 2013/0023992 A1 | 1/2013 | Moskowitz et al. |
| 2013/0023993 A1 | 1/2013 | Weiman |
| 2013/0023994 A1 | 1/2013 | Glerum |
| 2013/0030534 A1 | 1/2013 | DeLurio et al. |
| 2013/0030541 A1 | 1/2013 | Petit |
| 2013/0035724 A1 | 2/2013 | Fitzpatrick |
| 2013/0035763 A1 | 2/2013 | Krueger |
| 2013/0053962 A1 | 2/2013 | Moskowitz et al. |
| 2013/0073046 A1 | 3/2013 | Zaveloff |
| 2013/0079790 A1 | 3/2013 | Stein |
| 2013/0079793 A1 | 3/2013 | Stein |
| 2013/0085572 A1 | 4/2013 | Glerum et al. |
| 2013/0103153 A1 | 4/2013 | Blackwell et al. |
| 2013/0103156 A1 | 4/2013 | Packer et al. |
| 2013/0110248 A1 | 5/2013 | Zipnick |
| 2013/0123927 A1 | 5/2013 | Malandain |
| 2013/0158663 A1 | 6/2013 | Miller et al. |
| 2013/0158664 A1 | 6/2013 | Palmatier et al. |
| 2013/0158668 A1 | 6/2013 | Nichols et al. |
| 2013/0158669 A1 | 6/2013 | Sungarian et al. |
| 2013/0197642 A1 | 8/2013 | Ernst |
| 2013/0204371 A1 | 8/2013 | McLuen et al. |
| 2013/0211525 A1 | 8/2013 | McLuen et al. |
| 2013/0211526 A1 | 8/2013 | Alheidt |
| 2013/0253650 A1 | 9/2013 | Ashley et al. |
| 2013/0274883 A1 | 10/2013 | McLuen et al. |
| 2013/0310938 A1 | 11/2013 | Sournac et al. |
| 2013/0317554 A1 | 11/2013 | Purcell |
| 2014/0012383 A1 | 1/2014 | Triplett |
| 2014/0039622 A1 | 2/2014 | Glerum |
| 2014/0058521 A1 | 2/2014 | McLuen et al. |
| 2014/0066941 A1 | 3/2014 | Mignucci |
| 2014/0088708 A1 | 3/2014 | McLaughlin et al. |
| 2014/0094917 A1 | 4/2014 | Salemi |
| 2014/0114414 A1 | 4/2014 | Abdou |
| 2014/0121774 A1 | 5/2014 | Glerum |
| 2014/0143577 A1 | 5/2014 | Huffmaster |
| 2014/0148902 A1 | 5/2014 | Dickson |
| 2014/0156006 A1 | 6/2014 | Bannigan et al. |
| 2014/0156007 A1 | 6/2014 | Pabst |
| 2014/0156008 A1 | 6/2014 | Flickinger et al. |
| 2014/0180421 A1 | 6/2014 | Glerum |
| 2014/0214166 A1 | 7/2014 | Theofilos |
| 2014/0214167 A1 | 7/2014 | Theofilos |
| 2014/0236296 A1 | 8/2014 | Wagner et al. |
| 2014/0236297 A1 | 8/2014 | Lott |
| 2014/0243982 A1 | 8/2014 | Miller |
| 2014/0249629 A1 | 9/2014 | Moskowitz et al. |
| 2014/0257296 A1 | 9/2014 | Lopez |
| 2014/0257485 A1 | 9/2014 | Matthis et al. |
| 2014/0277470 A1 | 9/2014 | Baynham |
| 2014/0277490 A1 | 9/2014 | Perloff |
| 2014/0277500 A1 | 9/2014 | Logan et al. |
| 2014/0277504 A1 | 9/2014 | Forton et al. |
| 2014/0277509 A1 | 9/2014 | Robinson et al. |
| 2014/0277510 A1 | 9/2014 | Robinson |
| 2014/0288652 A1 | 9/2014 | Boehm et al. |
| 2014/0343677 A1 | 11/2014 | Davis et al. |
| 2014/0343678 A1 | 11/2014 | Suddaby et al. |
| 2014/0371754 A1 | 12/2014 | Buttler |
| 2015/0012097 A1 | 1/2015 | Ibarra |
| 2015/0018954 A1 | 1/2015 | Loebl |
| 2015/0018957 A1 | 1/2015 | Nicholas |
| 2015/0025633 A1 | 1/2015 | McLaughlin |
| 2015/0066031 A1 | 3/2015 | Lechoslaw |
| 2015/0066145 A1 | 3/2015 | Rogers |
| 2015/0094814 A1 | 4/2015 | Emerick et al. |
| 2015/0148906 A1 | 5/2015 | Sicotte |
| 2015/0148907 A1 | 5/2015 | Kleiner |

(56) References Cited

U.S. PATENT DOCUMENTS

| | | |
|---|---|---|
| 2015/0157496 A1 | 6/2015 | Prado |
| 2015/0190242 A1 | 7/2015 | Blain |
| 2015/0238327 A1 | 8/2015 | Cheng |
| 2015/0241925 A1 | 8/2015 | Seo et al. |
| 2015/0250606 A1 | 9/2015 | McLean |
| 2015/0250609 A1 | 9/2015 | McLean |
| 2015/0257894 A1 | 9/2015 | Levy |
| 2015/0272743 A1 | 10/2015 | Jimenez |
| 2015/0282797 A1 | 10/2015 | O'Neil et al. |
| 2015/0328013 A1 | 11/2015 | Barrall |
| 2015/0366675 A1 | 12/2015 | Matthew |
| 2015/0374507 A1 | 12/2015 | Wolters |
| 2015/0374509 A1 | 12/2015 | Spine |
| 2016/0015523 A1 | 1/2016 | Lewis |
| 2016/0022438 A1 | 1/2016 | Laborne |
| 2016/0030191 A1 | 2/2016 | McLuen et al. |
| 2016/0030195 A1 | 2/2016 | Prevost |
| 2016/0038305 A1 | 2/2016 | Weiman |
| 2016/0045326 A1 | 2/2016 | Hansen |
| 2016/0058575 A1 | 3/2016 | Sutterlin, III et al. |
| 2016/0089247 A1 | 3/2016 | Nicholas |
| 2016/0106551 A1 | 4/2016 | Grimberg, Jr. |
| 2016/0242932 A1 | 8/2016 | McLuen et al. |
| 2016/0256148 A1 | 9/2016 | Huffmaster |
| 2016/0256291 A1 | 9/2016 | Miller |
| 2016/0278933 A1 | 9/2016 | Selmer |
| 2016/0317323 A1 | 11/2016 | Cho |
| 2016/0354211 A1 | 12/2016 | Packer |
| 2016/0374735 A1 | 12/2016 | Bootwala |
| 2017/0000627 A1 | 1/2017 | Levy |
| 2017/0056197 A1 | 3/2017 | Weiman |
| 2017/0071750 A1 | 3/2017 | Urban |
| 2017/0071752 A1 | 3/2017 | McLuen et al. |
| 2017/0071753 A1 | 3/2017 | Josse |
| 2017/0100260 A1 | 4/2017 | Duffield |
| 2017/0119542 A1 | 5/2017 | Logan et al. |
| 2017/0119543 A1 | 5/2017 | Dietzel et al. |
| 2017/0202684 A1 | 7/2017 | Padovani |
| 2017/0215767 A1 | 8/2017 | Ziemek |
| 2017/0216050 A1 | 8/2017 | Semler |
| 2017/0224500 A1 | 8/2017 | Perloff |
| 2017/0245997 A1 | 8/2017 | Trischlet |
| 2017/0273804 A1 | 9/2017 | Emerick |
| 2017/0281365 A1 | 10/2017 | Robinson |
| 2017/0290671 A1 | 10/2017 | Milz |
| 2017/0304066 A1 | 10/2017 | Smith |
| 2017/0325969 A1 | 11/2017 | McLean |
| 2017/0333198 A1 | 11/2017 | Robinson |
| 2018/0014944 A1 | 1/2018 | Davis |
| 2018/0036137 A1 | 2/2018 | Levieux |
| 2018/0036138 A1 | 2/2018 | Robinson |
| 2018/0042735 A1 | 2/2018 | Schell |
| 2018/0049890 A1 | 2/2018 | Propejoy |
| 2018/0064551 A1 | 3/2018 | Stein |
| 2018/0116815 A1 | 5/2018 | Kuyler |
| 2018/0161175 A1 | 6/2018 | Frasier |
| 2018/0185163 A1 | 7/2018 | Weiman |
| 2018/0200075 A1 | 7/2018 | Baker et al. |
| 2018/0200076 A1 | 7/2018 | Knapp et al. |
| 2018/0200077 A1 | 7/2018 | Knapp et al. |
| 2018/0200078 A1 | 7/2018 | Remington et al. |
| 2018/0228622 A1 | 8/2018 | McLuen et al. |
| 2018/0263787 A1 | 9/2018 | McLuen et al. |
| 2018/0289506 A1 | 10/2018 | Kim |
| 2018/0293631 A1 | 10/2018 | Butler |
| 2018/0303530 A1 | 10/2018 | Kang |
| 2018/0318107 A1 | 11/2018 | Cummins |
| 2018/0344485 A1 | 12/2018 | McLuen et al. |
| 2019/0008649 A1 | 1/2019 | Logan et al. |
| 2019/0008658 A1 | 1/2019 | Knapp et al. |
| 2019/0083283 A1 | 3/2019 | Sharifi-Mehr et al. |
| 2019/0105183 A1 | 4/2019 | Adamo |
| 2019/0183656 A1 | 6/2019 | Besaw |
| 2019/0254841 A1 | 8/2019 | To |
| 2022/0104950 A1 | 4/2022 | Trudeau |
| 2022/0107207 A1 | 4/2022 | Suyderhoud |

FOREIGN PATENT DOCUMENTS

| | | |
|---|---|---|
| CN | 202165357 | 3/2012 |
| CN | 102429805 | 5/2015 |
| DE | 29911382 | 8/1999 |
| JP | 2274243 | 11/1990 |
| WO | WO9117723 | 11/1991 |
| WO | 2006047581 | 5/2006 |
| WO | 2006134262 | 12/2006 |
| WO | 2008035849 | 3/2008 |
| WO | 2008070863 | 6/2008 |
| WO | 2008086276 | 7/2008 |
| WO | 201006258 | 1/2010 |
| WO | 2010045301 | 4/2010 |
| WO | 2010121030 | 10/2010 |
| WO | 2011116136 | 9/2011 |
| WO | 2013023096 | 2/2013 |
| WO | 2013023098 | 2/2013 |
| WO | 2013025876 | 2/2013 |

OTHER PUBLICATIONS

International Search Report and Written Opinion dated Feb. 9, 2018 from International Application No. PCT/US2018/13644.
International Search Report and Written Opinion dated Feb. 9, 2018 from International Application No. PCT/US18/13715.
Search Report from European Application No. EP13797446 dated Jan. 26, 2016.
International Search Report and Written Opinion from International Application No. PCT/US2018/013394 dated Mar. 28, 2018.
International Search Report and Written Opinion from International Application No. PCT/US2018/13681 dated Apr. 5, 2018.
International Search Report and Written Opinion from International Application No. PCT/US18/013851 dated May 17, 2018.
International Search Report and Written Opinion from International Application No. PCT/US2018/013717 dated Mar. 7, 2018.
International Preliminary Examination Report from the International Application No. PCT/US2018/013681, dated Aug. 1, 2019.
International Preliminary Report from the International Application No. PCT/US2018/013394, dated Aug. 1, 2019.
International Preliminary Report from the International Application No. PCT/US2018/013715, dated Aug. 1, 2019.
International Preliminary Report from the International Application No. PCT/US2018/013717, dated Aug. 1, 2019.
International Preliminary Report from the International Application No. PCT/US2018/013851, dated Aug. 1, 2019.
International Preliminary Report from the International Application No. PCT/US2018/013644, dated Aug. 1, 2019.
The Second Office Action from the Chinese Application No. 201710881041.x, dated Jun. 26, 2019.
Australian Examination Report No. 1, from Australian Patent Application No. 2014236698.
First Examination Report fro the Indian application 2411/MUMNP/2014 dated Feb. 26, 2021.
The Office Action for the Chinese Application No. 20171088104.X dated Feb. 3, 2020.
The Office Action for the Korean Application No. 10-2014-7036320 dated Dec. 19, 2019.
The Notice of Hearing dated Nov. 9, 2023 issued in Indian Patent Application No. 2411/MUMNP/2014.
The Office Action from the Thai Patent Office that was mailed on Dec. 20, 2023 for Thailand Patent Application No. 1501000484.

\* cited by examiner

BONE FUSION DEVICE, APPARATUS AND METHOD

RELATED APPLICATIONS

This Application is a continuation of co-pending U.S. patent application Ser. No. 17/872,305, filed on Jul. 25, 2022 and entitled "BODILESS BONE FUSION DEVICE, APPARATUS AND METHOD," which is a continuation of U.S. patent application Ser. No. 16/789,128, filed on Feb. 12, 2020 and entitled "BODILESS BONE FUSION DEVICE, APPARATUS AND METHOD," which is a continuation of U.S. patent application Ser. No. 16/119,809, filed on Aug. 31, 2018 and entitled "BODILESS BONE FUSION DEVICE, APPARATUS AND METHOD," which is a divisional of U.S. patent application Ser. No. 14/210,094, filed on Mar. 13, 2014 and entitled "BODILESS BONE FUSION DEVICE, APPARATUS AND METHOD," which claims priority under 35 U.S.C. 119 (e) of the U.S. Provisional Application Ser. No. 61/794,789, filed Mar. 15, 2013, and entitled BODILESS BONE FUSION DEVICE, APPARATUS AND METHOD" and the U.S. Provisional Application Ser. No. 61/858,505, filed Jul. 25, 2013, and entitled BODILESS BONE FUSION DEVICE, APPARATUS AND METHOD," all of which are hereby incorporated by reference.

FIELD OF THE INVENTION

This invention relates generally to bone fusion devices. More specifically, the present invention relates to bodiless devices for fusing vertebrae of the spine or other bones.

BACKGROUND OF THE INVENTION

The spinal column is made up of vertebrae stacked on top of one another. Between the vertebrae are discs which are gel-like cushions that act as shock-absorbers and keep the spine flexible. Injury, disease, or excessive pressure on the discs can cause degenerative disc disease or other disorders where the disc becomes thinner and allows the vertebrae to move closer together or become misaligned. Similarly, vertebrae are able to weaken due to impact or disease reducing their ability to properly distribute forces on the spine. As a result, nerves may become pinched, causing pain that radiates into other parts of the body, or instability of the vertebrae may ensue.

One method for correcting disc and/or vertebrae-related disorders is to insert a fusion cage as a replacement for and/or in between the vertebrae to act as a structural replacement for the deteriorated disc and/or vertebrae. The fusion cage is typically a hollow metal device usually made of titanium. Once inserted, the fusion cage maintains the proper separation between the vertebrae to prevent nerves from being pinched and provides structural stability to the spine. Also, the inside of the cage is filled with bone graft material which eventually fuses permanently with the adjacent vertebrae into a single unit. However, it is difficult to retain this bone graft material in the cage and in the proper positions to stimulate bone growth.

The use of fusion cages for fusion and stabilization of vertebrae in the spine is known in the prior art. U.S. Pat. No. 4,961,740 to Ray, et al. entitled, "V-Thread Fusion Cage and Method of Fusing a Bone Joint," discloses a fusion cage with a threaded outer surface, where the crown of the thread is sharp and cuts into the bone. Perforations are provided in valleys between adjacent turns of the thread. The cage can be screwed into a threaded bore provided in the bone structure at the surgical site and then packed with bone chips which promote fusion.

U.S. Pat. No. 5,015,247 to Michelson entitled, "Threaded Spinal Implant," discloses a fusion implant comprising a cylindrical member having a series of threads on the exterior of the cylindrical member for engaging the vertebrae to maintain the implant in place and a plurality of openings in the cylindrical surface.

U.S. Pat. No. 6,342,074 to Simpson entitled, "Anterior Lumbar Underbody Fusion Implant and Method For Fusing Adjacent Vertebrae," discloses a one-piece spinal fusion implant comprising a hollow body having an access passage for insertion of bone graft material into the intervertebral space after the implant has been affixed to adjacent vertebrae. The implant provides a pair of screw-receiving passages that are oppositely inclined relative to a central plane. In one embodiment, the screw-receiving passages enable the head of an orthopaedic screw to be retained entirely within the access passage.

U.S. Pat. No. 5,885,287 to Bagby entitled, "Self-tapping Interbody Bone Implant," discloses a bone joining implant with a rigid, implantable base body having an outer surface with at least one bone bed engaging portion configured for engaging between a pair of bone bodies to be joined, wherein at least one spline is provided by the bone bed engaging portion, the spline being constructed and arranged to extend outwardly of the body and having an undercut portion.

U.S. Pat. No. 6,582,467 to Teitelbaum et al. entitled, "Expandable Fusion Cage," discloses an expandable fusion cage where the surfaces of the cage have multiple portions cut out of the metal to form sharp barbs. As the cage is expanded, the sharp barbs protrude into the subcortical bone of the vertebrae to secure the cage in place. The cage is filled with bone or bone matrix material.

U.S. Pat. No. 5,800,550 to Sertich entitled, "Interbody Fusion Cage," discloses a prosthetic device which includes an inert generally rectangularly shaped support body adapted to be seated on hard end plates of vertebrae. The support body has top and bottom faces. A first peg is movably mounted in a first aperture located in the support body, and the first aperture terminates at one of the top and bottom faces of the support body. Further, the first peg projects away from the one of the top and bottom faces and into an adjacent vertebra to secure the support body in place relative to the vertebra.

U.S. Pat. No. 6,436,140 to Liu et al. entitled, "Expandable Interbody Fusion Cage and Method for Insertion," discloses an expandable hollow interbody fusion device, wherein the body is divided into a number of branches connected to one another at a fixed end and separated at an expandable end. The expandable cage may be inserted in its substantially cylindrical form and may be expanded by movement of an expansion member to establish lordosis of the spine. An expansion member interacts with the interior surfaces of the device to maintain the cage in the expanded condition and provide a large internal chamber for receiving bone in-growth material.

These patents all disclose fusion cage devices that can be inserted between vertebrae of the spine in an invasive surgical procedure. Such an invasive surgical procedure requires a long recovery period.

SUMMARY OF THE INVENTION

The present application is directed to a bodiless bone fusion method, apparatus and device for insertion between bones that are to be fused together and/or in place of one or more of the bones, such as, for example, the vertebrae of a spinal column. The bodiless bone fusion device comprises one or more extendable plates, one or more extending blocks in communication with the extendable plates, one or more positioning elements for adjusting the extendable plates by manipulating the extending blocks, and one or more support panels for holding the positioning elements and guiding the extendable plates. The bodiless bone fusion device is able to be inserted between or replace the vertebrae by using a minimally invasive procedure. After the device has been positioned between the vertebrae, and the positioning elements are able to be rotated to position the plates. In particular, the plates are able to be positioned by rotating the positioning elements causing extending blocks to move and push outwards against the plates as the extending blocks approach the ends of the bodiless bone fusion device. In some embodiments, a single plate is extended. Thus, the plates are able to be advantageously positioned in the confined space between the vertebrae to help brace the device until the bone has fused.

A first aspect is directed to a bodiless bone fusion device for insertion into a desired location. The bodiless bone fusion device comprises an extending mechanism including one or more extending blocks mechanically coupled with a positioning element such that rotation of the positioning element causes the blocks to move with respect to the positioning element and a pair of plates straddling the extending mechanism and mechanically coupled with the extending blocks such that when the extending blocks move with respect to the positioning element, the plates move along a path with respect to each other between a retracted position in which the plates are adjacent to each other to an extended positioned in which the plates are spread apart from each other, wherein the plates are sized such that at least a portion of the perimeter of the plates about the path align with the outermost perimeter of the device about the path. In some embodiments, the plates are sized such that the entirety of the perimeter of the plates about the path align with the outermost perimeter of the device about the path. In some embodiments, the device further comprises one or more biasing elements physically coupled with both of the plates and positioned such that the biasing elements apply a force resisting the movement of the plates from the retracted position to the extended position. In some embodiments, the biasing elements have a shape selected from the group consisting of a ring, a C-shape and a ring-shaped coil. In some embodiments, the extending blocks each comprise an angled surface between a left side and a right side, wherein the left sides of the blocks are aligned with a left face of the plates and the right sides of the blocks are aligned with a right face of the plates. In some embodiments, angled surface forms a continuous sheet between the left and right sides of the blocks in order to increase the surface area of the angled surface. In some embodiments, the device further comprises a locking mechanism coupled with the positioning element and configured to physically bias the rotational orientation of the positioning element into one of a plurality of positions. In some embodiments, the locking mechanism comprises one or more stoppers each having a bump and a dial having one or more dimples and coupled with the positioning element such that the dial rotates with the positioning element, wherein the bumps do not rotate with the dial and the stoppers are positioned adjacent to the dial such that, when aligned, one or more of the bumps spring into one or more of the dimples. In some embodiments, the device further comprises one or more support panels coupled with the locking mechanism and the extending mechanism, wherein each of the support panels are positioned within a panel aperture on each of the plates such that as the plates move between the retracted and the extended positions the plates slide up or down the panels via the panels apertures. In some embodiments, at least one of the support panels comprises a pair of grip tabs that protrude from the sides of the support panel into a pair of grip apertures formed by the plates when the plates are in the retracted position.

A second aspect is directed to a method of implanting a bodiless bone fusion device into a desired location. The method comprises inserting the bodiless bone fusion device in the desired location, wherein the bodiless bone fusion device comprises an extending mechanism including one or more extending blocks mechanically coupled with a positioning element such that rotation of the positioning element causes the blocks to move with respect to the positioning element and a pair of plates straddling the extending mechanism and mechanically coupled with the extending blocks such that when the extending blocks move with respect to the positioning element, the plates move along a path with respect to each other between a retracted position in which the plates are adjacent to each other to an extended positioned in which the plates are spread apart from each other, wherein the plates are sized such that at least a portion of the perimeter of the plates about the path align with the outermost perimeter of the device about the path and moving the plates between the retracted position and the extended position with the extending mechanism. In some embodiments, the plates are sized such that the entirety of the perimeter of the plates about the path align with the outermost perimeter of the device about the path. In some embodiments, the bodiless bone fusion device further comprises one or more biasing elements physically coupled with both of the plates and positioned such that the biasing elements apply a force resisting the movement of the plates from the retracted position to the extended position. In some embodiments, the biasing elements have a shape selected from the group consisting of a ring, a C-shape and a ring-shaped coil. In some embodiments, the extending blocks each comprise an angled surface between a left side and a right side, wherein the left sides of the blocks are aligned with a left face of the plates and the right sides of the blocks are aligned with a right face of the plates. In some embodiments, the angled surface forms a continuous sheet between the left and right sides of the blocks in order to increase the surface area of the angled surface. In some embodiments, the bodiless bone fusion device further comprises a locking mechanism coupled with the positioning element and configured to physically bias the rotational orientation of the positioning element into one of a plurality of positions. In some embodiments, the locking mechanism comprises one or more stoppers each having a bump and a dial having one or more dimples and coupled with the positioning element such that the dial rotates with the positioning element, wherein the bumps do not rotate with the dial and the stoppers are positioned adjacent to the dial such that, when aligned, one or more of the bumps spring into one or more of the dimples. In some embodiments, the bodiless bone fusion device further comprises one or more support panels coupled with the locking mechanism and the extending mechanism, wherein each of the support panels are positioned within a panel aperture on each of the plates such that as the plates move between the retracted and extended positions the plates slide up or down the panels via the panels apertures. In some embodiments, at least one of the support panels comprises a pair of grip tabs that protrude from the sides of the support panel into a pair of grip apertures formed by the plates when the plates are in the retracted position.

DETAILED DESCRIPTION

In the following description, numerous details and alternatives are set forth for purpose of explanation. However, one of ordinary skill in the art will realize that the invention can be practiced without the use of these specific details. For instance, the figures and description below often refer to the vertebral bones of a spinal column. However, one of ordinary skill in the art will recognize that some embodiments of the invention are practiced for the fusion of other bones, including broken bones and/or joints. In other instances, well-known structures and devices are shown in block diagram form in order not to obscure the description of the invention with unnecessary detail.

Figure 1A:
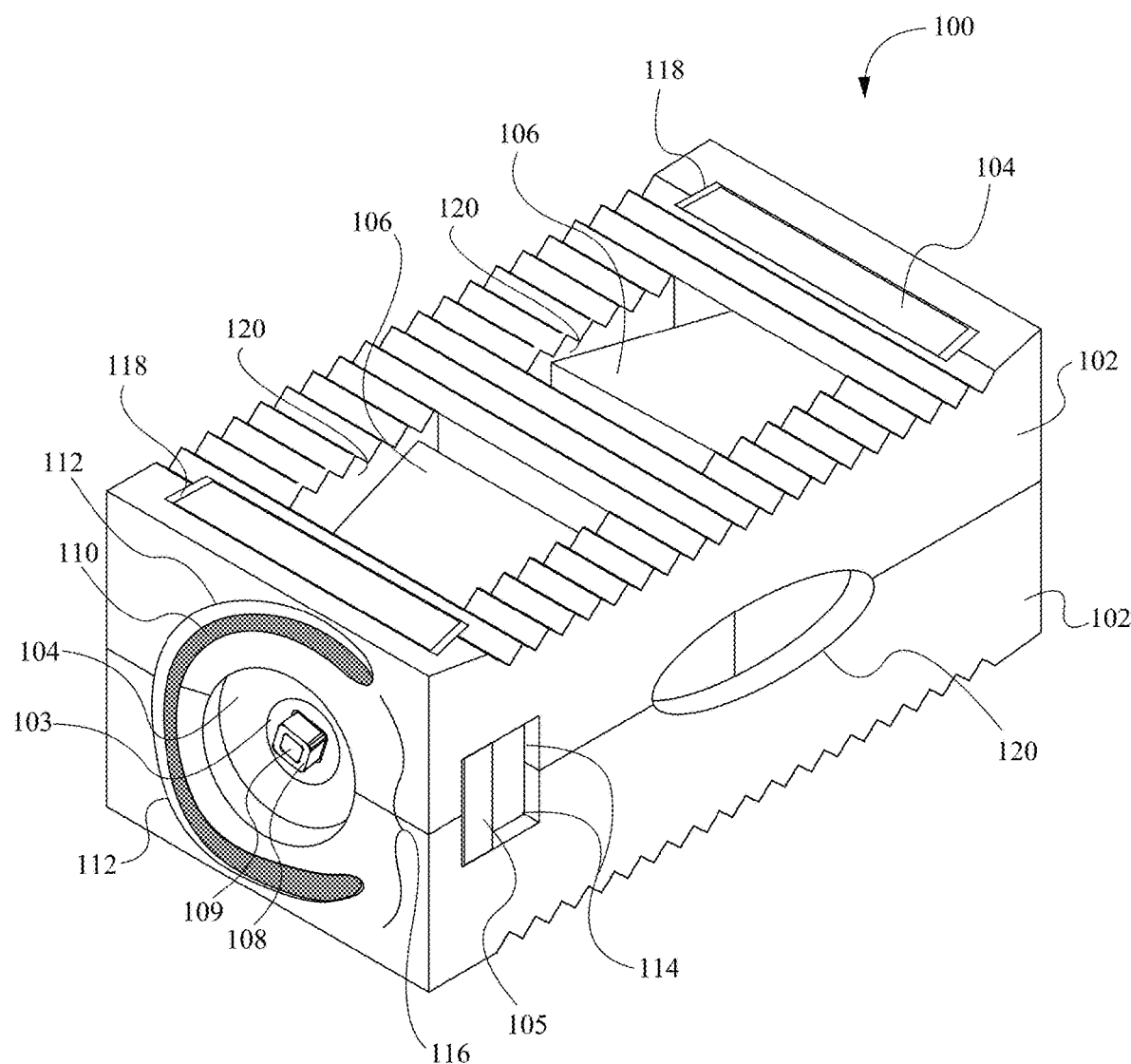
FIG. 1A illustrates a retracted perspective view of a bodiless bone fusion device according to some embodiments.
Figure 1B:
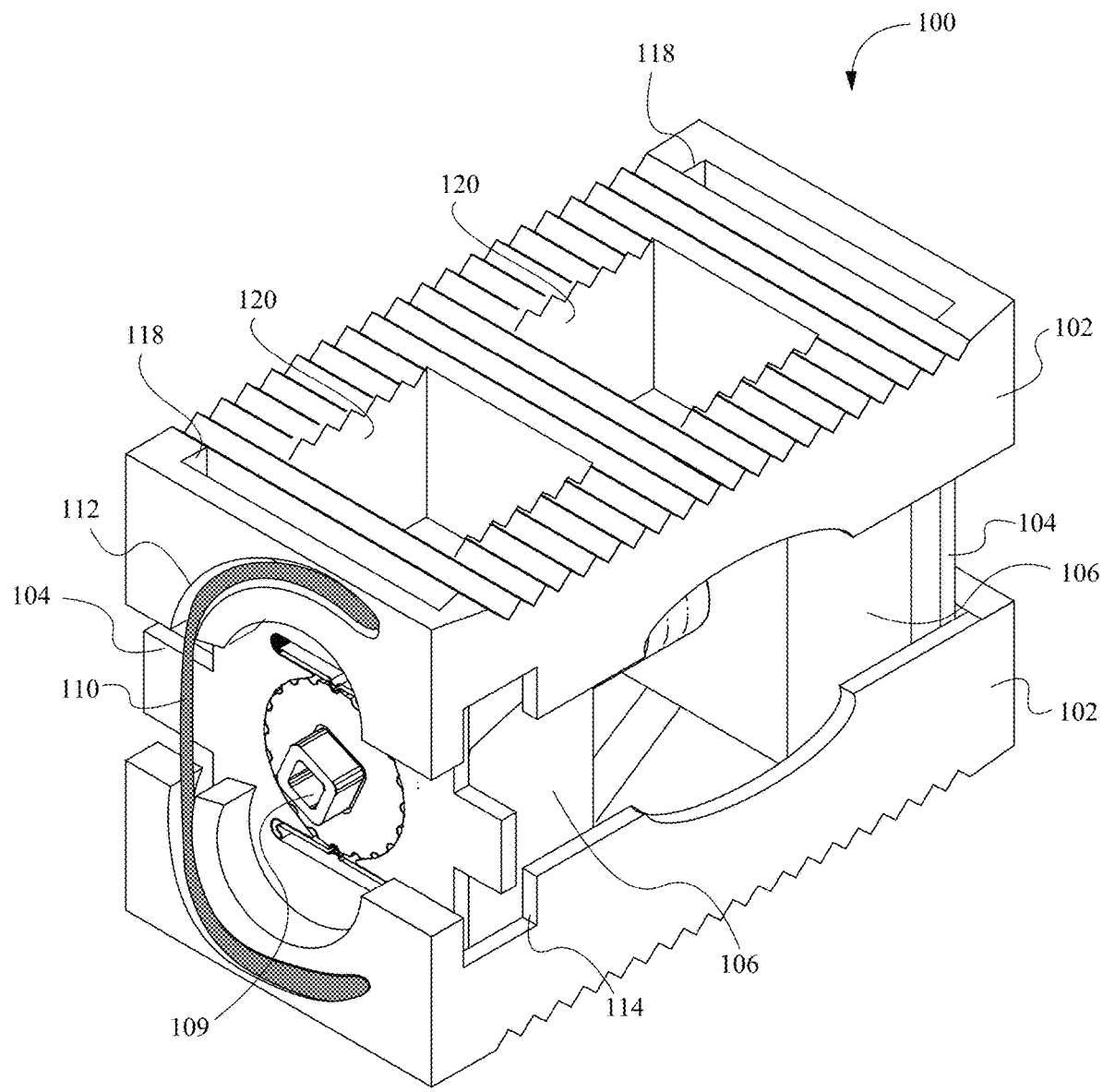
FIG. 1B illustrates an extended perspective view of a bodiless bone fusion device according to some embodiments.

FIGS. 1A and 1B illustrate retracted and extended perspective views, respectively, of a bodiless bone fusion device 100 according to some embodiments. The bodiless bone fusion device 100 is able to be constructed from a high strength biocompatible material, such as titanium, which has the strength to withstand compressive and shear forces in the spine that are generated by a patient's body weight and daily movements. Alternatively, part of all of the bodiless bone fusion device 100 is able to be constructed from one or more of the group consisting of high strength biocompatible material or a polymer such as PEEK, PEKK, and other polymeric materials know to be biocompatible and having sufficient strength. In some embodiments, the materials used to construct the bodiless bone fusion device include using additives, such as carbon fibers for better performance of the materials under various circumstances. The base biocompatible material is often textured or coated with a porous material conducive to the growth of new bone cells on the bodiless bone fusion device 100.

The bodiless bone fusion device 100 is able to have several conduits or holes 120 which permit the bone graft material to be inserted into the device 100 and to contact the vertebral bone before or after the device 100 has been inserted between the vertebrae of the patient. In particular, one or more holes 120 are able to be positioned on the lateral faces of the device 100 through one or both of the plates 102 such that the bone graft material is able to be inserted into the open spaces within the device 100 when the device is in the contracted position. It is understood that although only one conduit 120 on a lateral face is shown in FIG. 1A, any number of conduits 120 on lateral faces or other parts of the device 100 is contemplated. The bone graft material and the surface texturing of the device 100 encourage the growth and fusion of bone from the neighboring vertebrae. The fusion and healing process will result in the bodiless bone fusion device 100 aiding in the bridging of the bone between the two adjacent vertebral bodies of the spine which eventually fuse together during the healing period.

As shown in FIGS. 1A and 1B, the bodiless bone fusion device 100 comprises one or more extendable plates 102, one or more support panels 104, one or more extending blocks 106, one or more positioning elements 108 and one or more biasing elements 110. The positioning element 108 is rotatably positioned within panel apertures 103 of the support panels 104 and operably coupled with the one or more extending blocks 106. The support panels 104 are slidably positioned within plate apertures 118 of the extendable plates 102 and within a grip channel 114 of the extendable plates 102 when the device 100 is in the retracted position as shown in FIG. 1A. The biasing element 110 is positioned within biasing channels 112 on one or both ends of the extendable plates 102. In some embodiments, one or more of the holes 120, the grip channels 114, the biasing elements 110 and/or biasing channels 112 are able to be omitted. In some embodiments, one or more additional components are able to be added as are well known in the art. Additionally, it is noted that although FIGS. 1A and 1B only show two plates 102, a single positioning element 108, two extending blocks 106, two support panels 104 and two biasing elements 110, any number of plates 102, positioning elements 108, extending blocks 106, support panels 104 and/or biasing elements 110 is contemplated.

The one or more extending blocks 106 each are able to comprise a threaded conduit 122 for operably coupling to the positioning elements 108. In particular, as described below, the positioning elements 108 are able to comprise a plurality of threaded screws having different diameters wherein the threaded conduits 122 of the extending blocks 106 are able to be configured to screw onto or otherwise engage with one of the threaded screws of the positioning elements 108. Alternatively, one or more of the screws are able to have the same diameter. Further, each of the extending blocks 106 are able to comprise angled upper and/or lower outer surfaces for contacting/engaging angled inner surfaces 123 (see FIGS. 3A and 3B) of the extending plates 102. Specifically, the angled outer surfaces are able to be configured such that as the blocks 106 move along the positioning element 108 the angles outer surfaces push against the angled inner surfaces 123 causing the plates 102 to move outwards.

Figure 8:
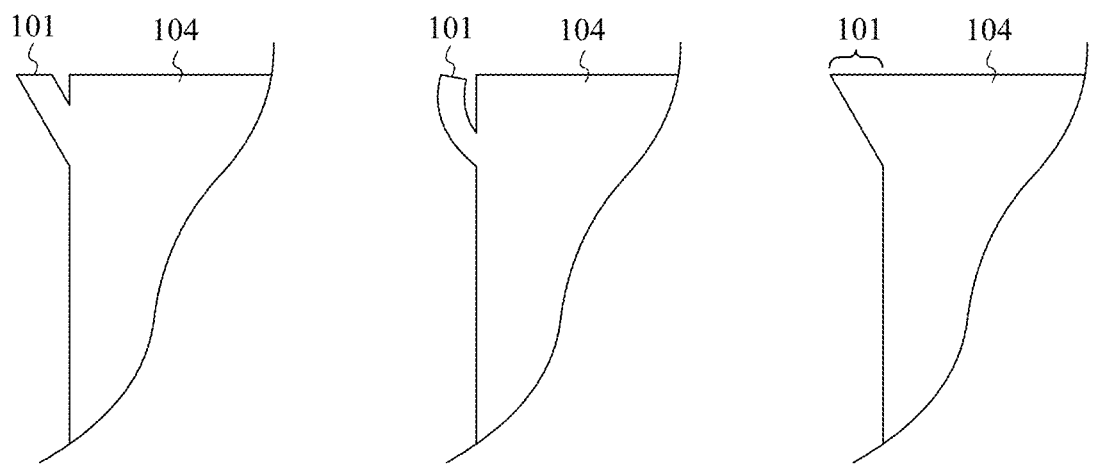
FIG. 8 illustrates a close-up view of support panels having retention tips according to some embodiments.

The support panels 104 are able to be sized/configured to slidably fit within one or more plate apertures 118 within the extendable plates 102. In some embodiments, one or more of the plate apertures 118 extend completely through the corresponding plate 102. Alternatively, one or more of the plate aperture 118 are able to only extend partially through the corresponding plate 102. When in the retracted position, the top and bottom portions of the support panels 104 are able to be positioned fully within a plate aperture 118 of each of the extendable plates 102 (e.g. such that the edge of the support panels 104 is substantially flush with the surface of the plates 102 if the plate aperture 118 extends through the top of the plate 102). As the plates 102 are extended outward to the extended position, the plates 102 slide up the panels 104, but the panels 104 remain at least partially within the plate apertures 118 even when in the fully extended position. In some embodiments, as shown in FIG. 8, the top and/or bottom of the panels 104 comprise one or more retention tips 101 that bow out or otherwise protrude out from the top and/or bottom of the panels 104 in order to block or mechanically stop the plates 102 from sliding off the top of the panels 104. For example, the retention tips 101 are able to extend out from the panels 104 and if the plates 102 slide up to the retention tips on the panel 104, the tips 101 provide a biasing force that pushes the plates 102 back down the panels 104 until they no longer contact the retention tips 101. Alternatively, other types of fasteners or stopping mechanisms are able to be used to prevent the plates 102 from sliding of the panels 104 as are well known in the art.

As a result, the panels 104 are able to maintain the alignment of the plates 102 with each other and with the positioning element 108 and extending blocks 106. Also, as described above, the support panels 104 are each able to comprise one of the panel apertures 103 such that the panels 104 are able to receive one end of the positioning element 108. Specifically, the panel apertures 103 are able to be configured to receive a non-threaded portion of an end of the positioning element 108 such that the positioning element 108 is held in place relative to the support panels 104, but allowed to rotate within the panel apertures 103. One or more of the support panels 104 are also able to comprise one or more grip tabs 105 that extend out the sides of the support panels 105. As described below, the grip tabs 105 are configured to fit within the grip channels 114 of the plates 102 and provide a gripping point to an insertion instrument used to insert and otherwise manipulate the device 100. In some embodiments, the grip tabs 105 comprise one or more indentations, conduits and/or fasteners for receiving detachably coupling with an insertion tool. For example, the grip tabs 105 are able to be configured such that they create a profile that matches the profile of the insertion tool such that the tool is able to securely grip the device 100 via the grip tabs 105.

The extendable plates 102 are able to be located on opposite sides of the device 100 and face is opposite directions. Internally, the plates 102 are able to have one or more angled inner surfaces 123 (see FIGS. 3A and 3B) that have end thicknesses that are larger than their middle thicknesses such that the thickness of the angled surfaces 123 gradually increases while going from the middle to the ends of the plate 102. Alternatively, the angled inner surfaces 123 are able to be configured such that they have end thicknesses that are smaller than their middle thicknesses such that the thickness of the angled surfaces 123 gradually decreases while going from the middle to the ends of the plate 102. In either configuration, the angles surfaces 123 are able to interact with the extending blocks 106 to cause the plates 102 to retract or extend between the retracted and extended positions. As described above, the plates 102 each comprise one or more plate apertures 118 that are sized to slidably receive the top or bottom of the support panels 104. As a result, the panels 104 are able to keep the plates 102 in alignment with each other as the plate 102 slide up and down along the support panels 104. Additionally, in some embodiments the panels 104 are able to be shaped similar to the grip tabs 105 and/or other shapes such that the panels 104 are able to both support the plates 102 as well as enable the plates 102 to slide along the panels 104.

Figure 2:
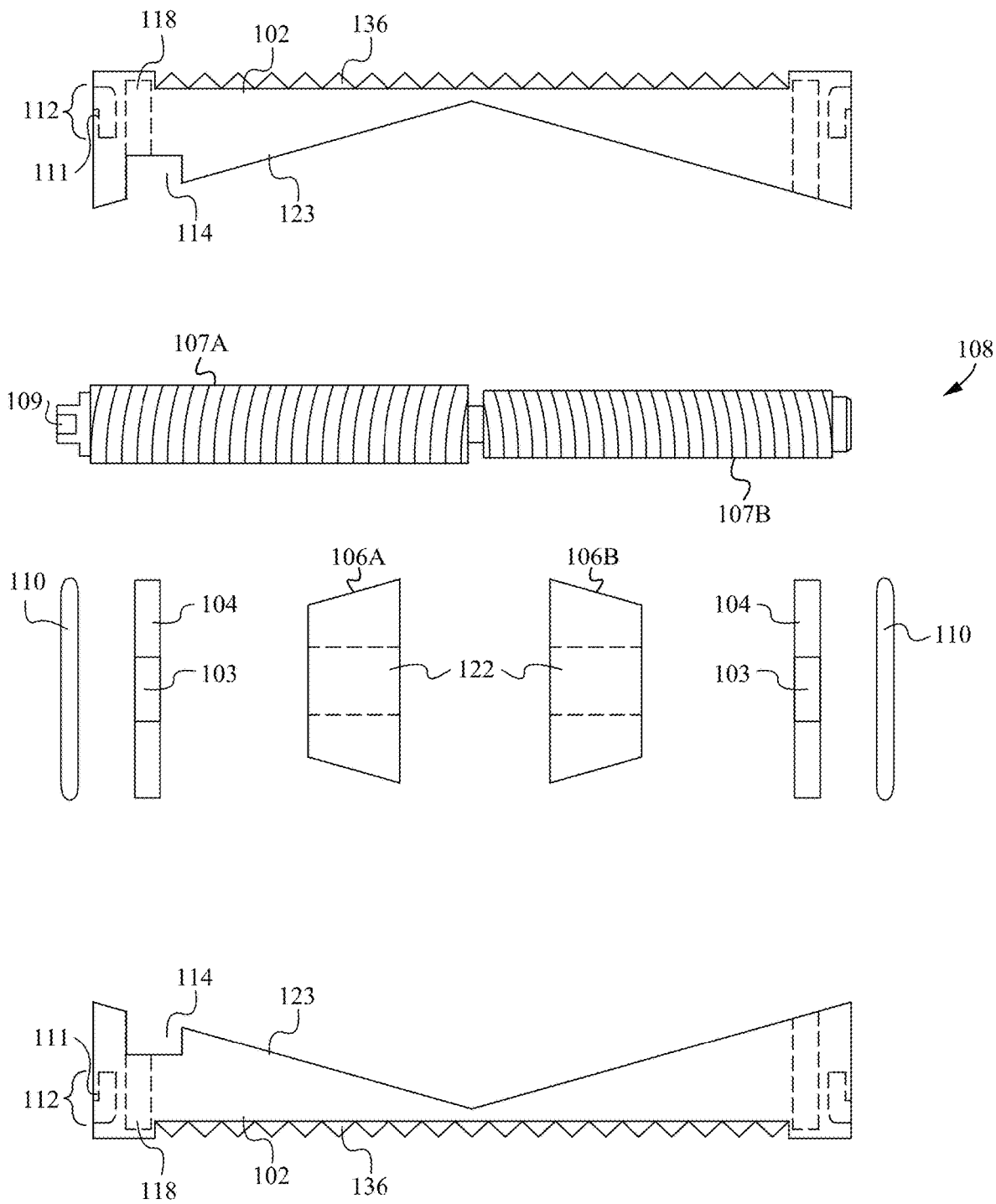
FIG. 2 illustrates a cross-sectional view of components of the bodiless bone fusion device according to some embodiments.

As also described above, the plates 102 each able to comprise the one or more biasing channels 112. In particular, the biasing channels 112 are able to be configured such that when the device 100 is in the retracted position the biasing channels 112 of the plates 102 align to form a continuous channel that crosses between the plates 102. In some embodiments, the biasing channels 112 are able to align at two or more positions between the plates 102 to form a continuous loop or other shape that crosses multiple times between the plates 102. In some embodiments, the biasing channels 112 include a lip guard 111 that holds the biasing elements 110 within the biasing channels 112. Alternatively, the biasing channels 112 are able to comprise coupling elements (not shown) that enable the biasing elements 110 to directly couple to the biasing channels 112 in order to stay within the channels 112. Although as shown in FIG. 2 the lip guard 111 is substantially straight forming a square-like channel 112, it is contemplated that the guard 111 is able to be angled, rounded, indented or otherwise shaped such that the guard 111 is able to retain the biasing elements 110 within the biasing channels 112. Further, the biasing channels 112 are able to each include one or more portions that are nonparallel to the direction in which the plates 102 are able to be extended in order to fit a biasing element 110 that provides resistance to the extension of and biases the plates 102 in the retracted position. In some embodiments, as shown in FIGS. 1A and 1B the biasing channels 112 form a C shape. Alternatively, the biasing channels 112 are able to form a loop (see FIGS. 6A-6C), snake or other shapes having nonparallel portions as are well known in the art. Alternatively, the biasing channels 112 are able to be entirely parallel but be coupled to the biasing element 110 such that a nonparallel portion is unnecessary to provide the force resisting extension of the plates 102. In some embodiments, the biasing channels 112 are positioned on the ends of the plates 102 as shown in FIGS. 1A and 1B. Alternatively, one or more of the biasing channels 112 are able to be positioned on another lateral face or faces of the plates 102.

Additionally, the plates 102 are able to have serrated edges or teeth 136 to further increase the bodiless bone fusion device's gripping ability and therefore ability to be secured in place between the bones for both a long-term purchase and a short-term purchase. In some embodiments, the serrated edges or teeth 136 are able to be in a triangular or form a triangular wave formation as shown in FIG. 2. Alternatively, the serrated edges or teeth are able to be filleted, chamfered, or comprise other teeth shapes or edge waves as are well known in the art. As described above, the plates 102 are able to comprise the grip channels 114 positioned on opposite sides of one or more ends of the plates 102. The grip channels 114 are able to be configured such that when the device 100 is in the retracted position the grip channels 114 of the plates 102 align and are partially filled by grip tabs 105 of the support panels 105. The remainder of the grip channels 114 is able to be configured to receive gripping fingers of an insertion instrument (not shown). In particular, the grip channels 114 enable the insertion instrument to grip the grip tabs 105 of one of the support panels 104 to manipulate the device 100 and to prevent the device 100 from slipping or during insertion into a patient. Alternatively, the grip tabs 105 are able to comprise one or more screw holes or other types of fasteners for fastening to an insertion instrument as are well known in the art.

Finally, the plates 102 are able to be configured such that when in the retracted position the extendable plates 102 house or surround the remainder of the components of the device 100. As a result, the bodiless bone fusion device 100 provides the advantage of maximizing the plate size to device size ratio because the size of the plates 102 is equal to the size of the device 100 in the retracted position creating a 1 to 1 ratio. This enables the device 100 to incorporate larger plates 102 that increase stability and surface area, which would not be possible with devices that incorporate a body. Additionally, it should be noted that one or more of the plates 102 are able to be non-flat, non-parallel to each other, or otherwise non-uniform. For example, one or more of the plates 102 are able to be partially or fully concave, convex and/or angled. Further, in some embodiments one or more of the plates 102 are able to be adjustable or interchangeable such that they enable adjustments to their surface/body shape.

The positioning element 108 is able to comprise a positioning aperture 109, a first screw 107A and a second screw 107B coupled together (see FIG. 2). The positioning aperture 109 is configured to receive a drive/engaging mechanism of a tool (not shown) such that the tool is able to rotate the positioning element 108. The positioning aperture 109 is able to comprise numerous shapes and sizes as are well known in the art. Alternatively, the positioning aperture 109 is able to be omitted and/or the end of the positioning element 108 is able to be shaped to fit within the drive/engaging mechanism of the tool. The first screw 107A is threaded opposite of the second screw 107B. For example, if the first screw 107A is left threaded, the second screw 107B is right threaded or vice versa. Furthermore, the first screw 107A is of a slightly different size than the second screw 107B. As described above, the positioning element 108 is able to be operably coupled to one or more of the extending blocks 106. For example, a first one of the extending blocks 106 is able to be threaded onto the first screw 107A and a second one of the extending blocks 106 is able to be threaded on to the second screw 107B.

When coupled to the positioning element 108, the extending blocks 102 are able to be positioned in the middle of the bodiless bone fusion device 100 in the retracted position. When the positioning element 108 is turned appropriately, the extending blocks 106 each travel outwardly on their respective screws 107A and 107B. As the extending blocks 106 travel outwardly, they push the angles surfaces 123 of the plates 102 causing the plates 102 to extend outward along the support panels 104. In other words, the inner plate surface 123 when in contact with the extending blocks 106 act in such a manner so as to push the respective plates 102 apart. Thus, the plates 102 will be fully extended when the extending blocks 106 reach the opposite ends of the screws 107A, 107B. To retract the plates 102, the positioning device 108 is turned in the opposite direction and the extending blocks 106 will each travel back to the middle on their respective screws 107A and 107B. It is contemplated that the operation of the device 100 is able to be reversed such that the plates 102, extending blocks 106, and positioning element 108 are configured such that the extending blocks 106 travel inwardly to extend the plates 102 into the extended position and travel outwardly to retract the plates 102 into the compact position. In any case, the nonextended plates 102 of the bodiless bone fusion device 100 provide a compact assembly that is suitable for insertion into the patient's body through a open, or minimally invasive surgical procedure. As used herein, an open or a minimally invasive procedure comprises a procedure wherein a smaller surgical incision is employed as compared to the size of the incision required for conventional invasive surgery, for example arthroscopic procedures. Moreover, minimally invasive procedures minimize or eliminate the need for excessive retraction of a patient's tissues such as muscles and nerves, thereby minimizing trauma and injury to the muscles and nerves and further reducing the patient's recovery time.

Figure 6A:
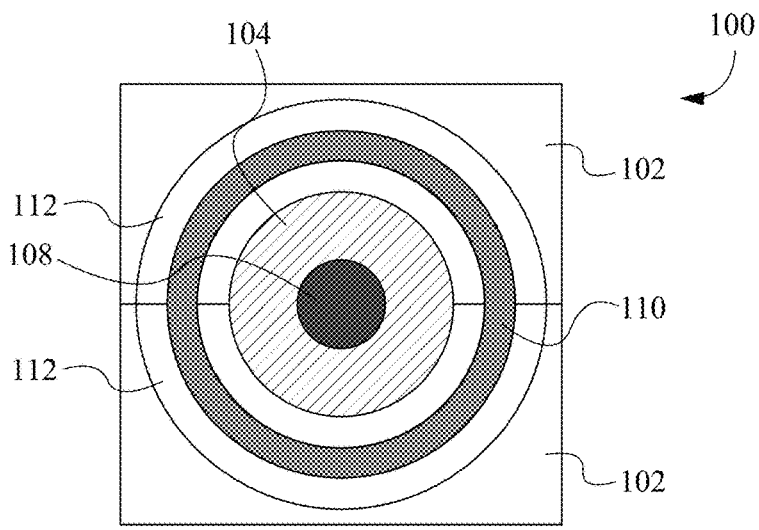
FIG. 6A illustrates a front view of the bodiless bone fusion device having a loop biasing element according to some embodiments.
Figure 6B:
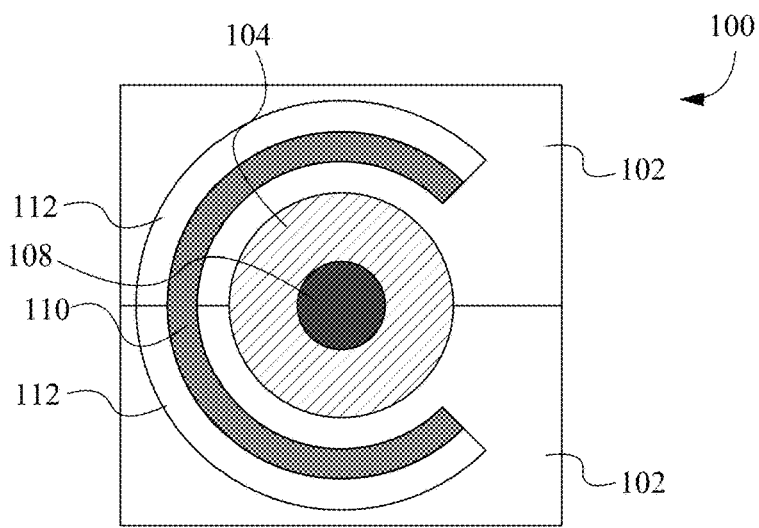
FIG. 6B illustrates a front view of the bodiless bone fusion device having a C shape biasing element according to some embodiments.
Figure 6C:
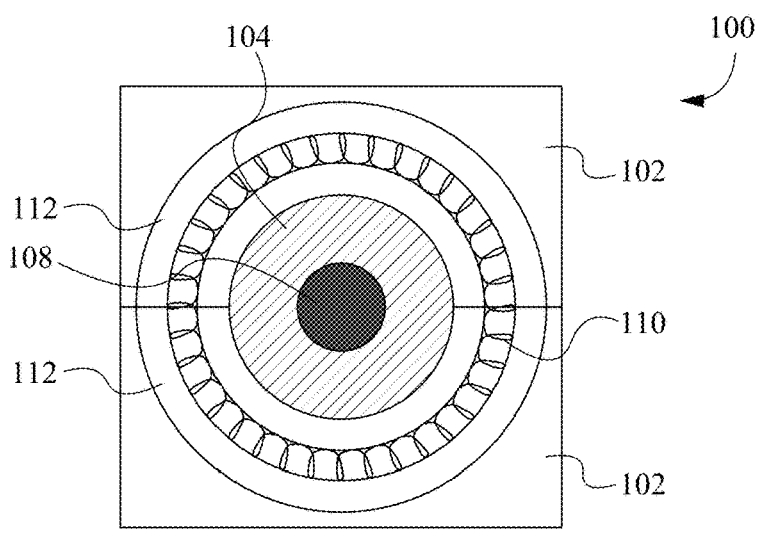
FIG. 6C illustrates a front view of the bodiless bone fusion device having a garter spring biasing element according to some embodiments.

The biasing elements 110 are able to be configured to fit within the biasing channels 112 of two or more plates 102 when the plates 102 are in alignment. For example, as shown in FIGS. 1A, 1B and 6B, one or more of the biasing elements 110 are able to shaped in a C shape or broken loop shape. Alternatively, as shown in FIG. 6A, one or more of the biasing elements 110 are able to have a circular, oval or loop shape. Alternatively, as shown in FIG. 6C, one or more of the biasing elements 110 are able to have a garter spring shape or any other type of shape formed by the biasing channels 112. Further, the biasing element 110 are able to be shaped to fit behind the lip guard 111 such that the lip guard 111 holds the biasing element 110 in place within the biasing channels 112. Alternatively, the biasing element 110 is able to directly couple to the plates 102 in order to stay within the biasing channels 112. In some embodiments, the biasing elements 110 are able to be structured and/or positioned such that their body blocks the extension of the plates 102 and thus the extension of the plates 102 causes deformation and/or stretching of the body of the biasing elements 110. As a result, the body deformation and/or stretching resistence of the biasing elements 100 provides an extension-resisting force that biases the plates 102 in the retracted position. This biasing provides the advantage of ensuring that the plates 102 remain in contact with extending blocks 106 as the plates 102 are extended and/or retracted. In some embodiments, one or more of the biasing elements 110 comprise nitinol to provide the deformation resistant and/or flexible structure. Alternatively, the biasing elements 110 are able to comprise other material having deformation resistant, springing and/or elastic properties as are well known in the art.

FIG. 2 illustrates a cross-sectional view of components of the bodiless bone fusion device 100 according to some embodiments. As shown in FIG. 2 and described above, the positioning element 108 is able to comprise a first screw 107A and a second screw 107B wherein the first screw 107A is threaded differently than that of the second screw 107B and is a different size than the second screw 107B. For example, in some embodiments the first screw 107A is an 8-32 screw and the second screw is a 6-32 screw. A first extending block 106A and a second extending block 106B are utilized with the positioning element 108 to extend and retract one or more of the plates 107A with respect to each other and/or the positioning element 108. The first extending block 106A has an internal opening and threading to fit around the first screw 107A. The second extending block 106B has an internal opening and threading to fit around the second screw 107B. The support panels 104 are coupled with the positioning element 108 via the plate apertures 118 of the plates 102. Specifically, because the plate apertures 118 receive the ends of the support panels 104, they prevent the panel apertures 103 of the support panels 104 from moving axially with respect to the positioning element 108 thereby keeping the ends of the positioning element 108 within the panel apertures 103. Further, the plates 102 are each coupled with each other via the support panels 104 that maintain the alignment of the plates 102 and the biasing elements 110 that hold the plates 102 onto the support panels 104.

Figure 3A:
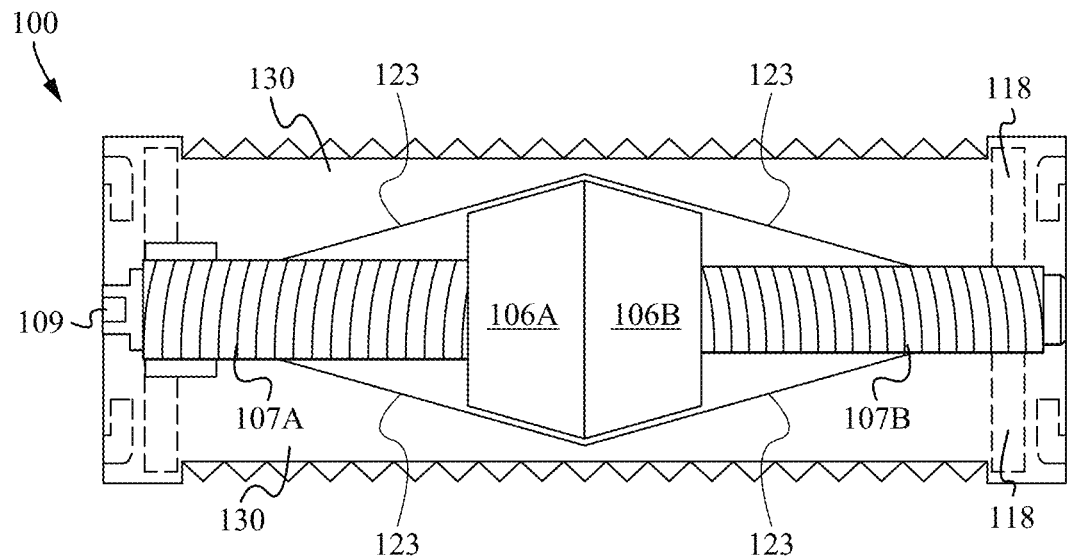
FIG. 3A illustrates a profile view of the bodiless bone fusion device with the plates retracted according to some embodiments.
Figure 3B:
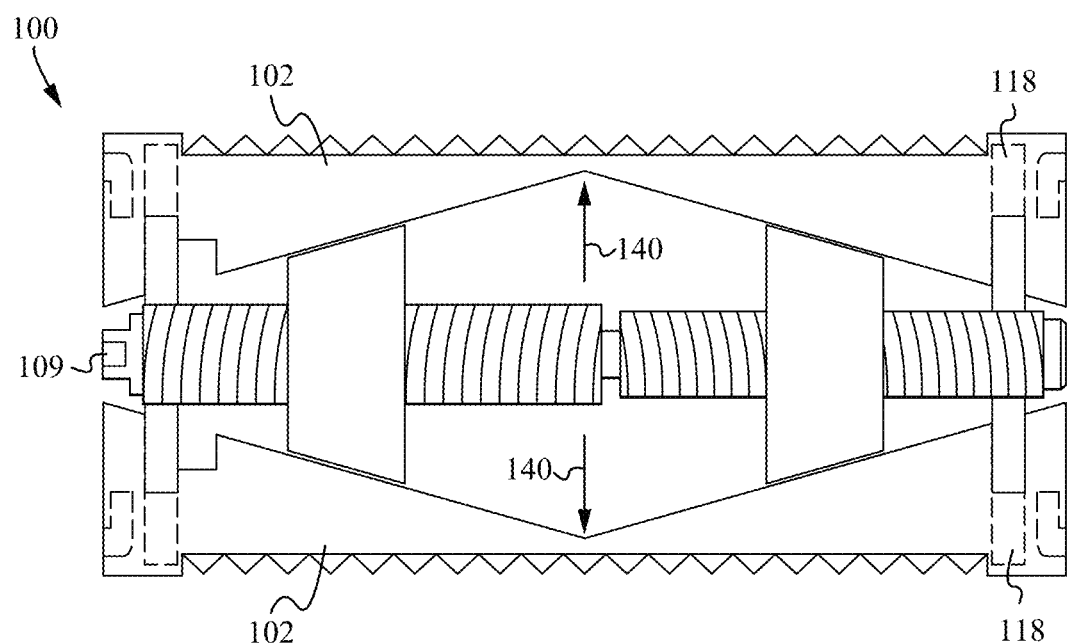
FIG. 3B illustrates a profile view of the bodiless bone fusion device with the plates extended according to some embodiments.

FIG. 3A illustrates a profile view of the bodiless bone fusion device 100 with the plates 102 retracted according to some embodiments. When the extending blocks 106 are positioned in the middle of the positioning element 108 with the first screw 107A and the second screw 107B, the plates 102 are positioned adjacent and/or in contact with each other. FIG. 3B illustrates a profile view of the bodiless bone fusion device 100 with the plates 102 extended according to some embodiments. As shown in FIG. 3A, the bodiless bone fusion device 100 is compressed/retracted when the extending blocks 106 are in the middle of the bodiless bone fusion device 100. As a user rotates the positioning element 108 via the positioning aperture 109, the extending blocks 106 gradually move outward from the middle. If the user turns the positioning element 108 in the opposite direction, the extending blocks move back towards the middle. As the extending blocks 106 are moving outward, the extending blocks 106A, 106B push on inner angles surfaces 123 of the plates 102. The plates 102 extend because the extending blocks 106 exert force against the angled inner surfaces 123 of the plates 102 outwardly as shown by the arrows 140. When the extending blocks 106 are positioned near the ends of the bodiless bone fusion device 100, the plates 102 extend beyond the outer edges of the ends of the support panels 104 of the bodiless bone fusion device 100 and ultimately secure the bodiless bone fusion device 100 between two bones.

In operation, the bodiless bone fusion device 100 is initially configured in a compact position such that the extending blocks 106A, 106B are located in the middle of the bodiless bone fusion device 100 thereby allowing the plates 102 to contact each other and/or the edges of the ends of the support panels 104 to be substantially flush with the outer surfaces of the plates 102 through the plate apertures 118. The compact bodiless bone fusion device 100 is then inserted into position within the patient and surgeon is able to expand the bodiless bone fusion device 100 by rotating the positioning element 108 which moves the extending blocks 106A, 106B towards the opposing ends of the bodiless bone fusion device 100—one near the head of the positioning element 108 and the other towards the tail of the positioning element 108. As the extending blocks 106A, 106B move away from the middle, the plates 102 are pushed outwardly from the pressure of the extending blocks 106A, 106B against the angled inner surfaces 123. Eventually the extending blocks 106A, 106B exert a satisfactory force between the extended plates 102 and the bones to be fused. At that point the bodiless bone fusion device 100 is able to remain in place. If the plates 102 are extended too far, the surgeon is able to rotate the positioning element 108 in the opposite direction moving the extending blocks 106A, 106B back towards the middle. At the same time, the biasing elements 110 exert a retraction force in the opposite direction of the force 140 that ensures the plates 102 retract as the extending blocks 106A, 106B move back towards the middle of the device 100. In particular, the retraction force is able to be applied to the plates 102 by biasing elements 110 throughout operation of the device 100 in order to both keep the plates 102 from sliding off the support panels 104 and keep the plates 102 in contact with the extending blocks 106 as the blocks 106 move along the positioning element 108. Thereafter, material for fusing the bones together is inserted through the holes and openings 120 within the bodiless bone fusion device 100. Alternatively, the insertion of the material for fusing the bones together is able to be omitted.

Figure 4:
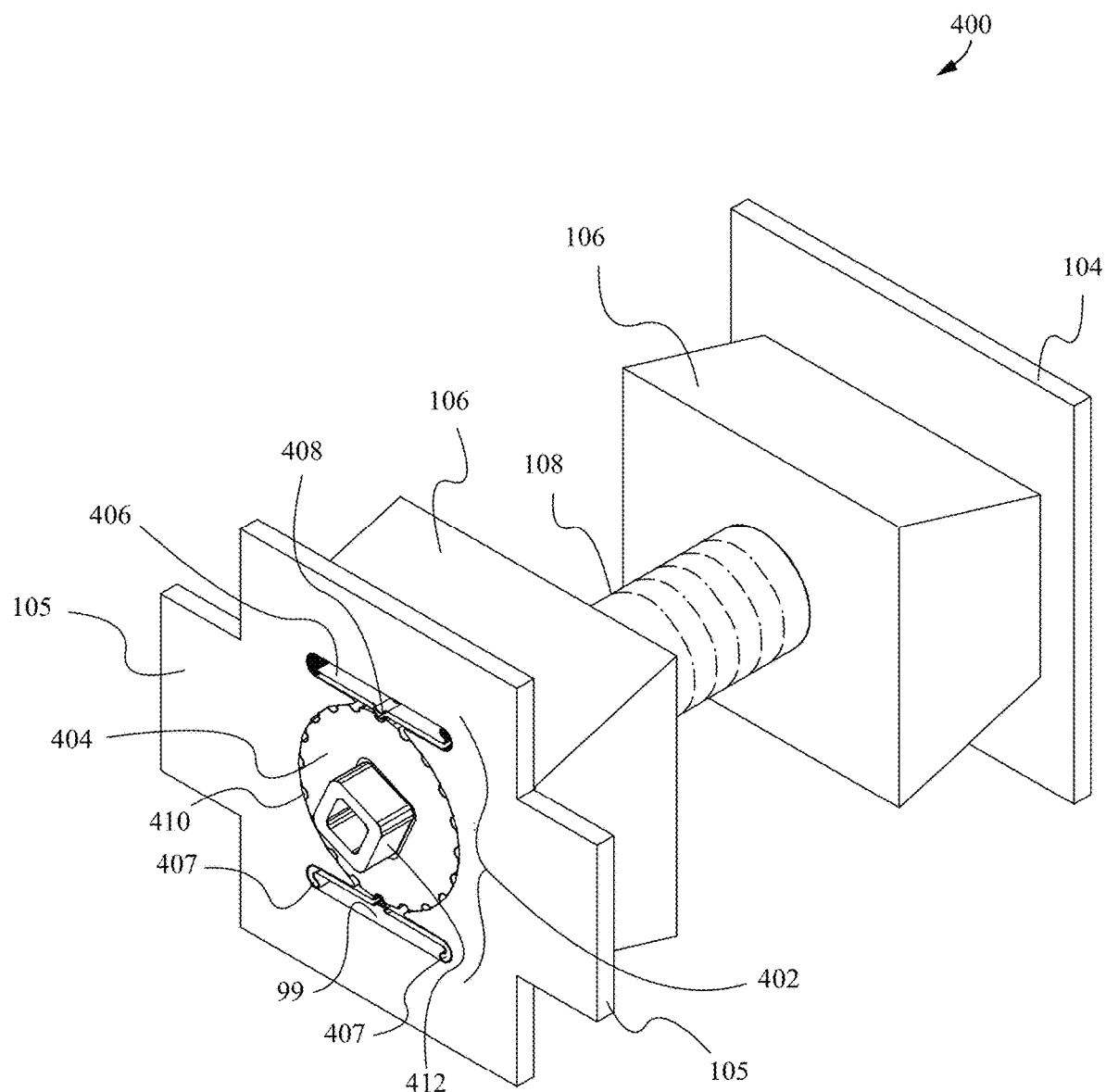
FIG. 4 illustrates a bodiless bone fusion device having a position locking mechanism according to some embodiments.

FIG. 4 illustrates a bodiless bone fusion device 400 having a position locking mechanism 402 according to some embodiments. The bodiless bone fusion device 400 shown in FIG. 4 is substantially similar to the bodiless bone fusion device 100 except for the differences described herein. It is noted that the plates 102 of the bone fusion device 400 have been omitted from FIG. 4 for the sake of clarity. As shown in FIG. 4, at least one of the support panels 104 comprises one or more additional panel apertures 99 configured to receive a position locking mechanism 402, wherein the position locking mechanism 402 comprises one or more dials 404 and one or more stoppers 406. The dial 404 is configured to rotatably fit within the panel apertures 99 and comprises a dial aperture 412 and one or more dimples 410 along the edge or perimeter of the dial 202. The dial aperture 412 is able to be sized or otherwise configured to receive an end of the positioning element 108 such that if the positioning element 108 is within the dial aperture 412, the end of the positioning element 108 will cause the dial 404 to rotate along with the positioning element 108. In some embodiments, the positioning element 108 causes the dial 404 to rotate by directly physically contacting the dial aperture 412. Alternatively, the positioning element 108 is able to cause the dial 404 to rotate via indirect contact. The one or more dimples 410 are able to be configured to receive one or more bumps 408 of the stoppers 406. In particular, the dimples 410 are able to have concave dimensions that substantially match convex dimensions of the bumps 408. The stoppers 406 are able to be configured to fit within the panel apertures 99 adjacent to the dial 404 and comprise one or more bumps 408. The stoppers 406, dials 404 and apertures 99 are configured such that when within the apertures 99, the stoppers 406 are adjacent or in contact with the dial 404 and the bumps 408 of the stoppers 406 snap or spring fit within the dimples 410 of the dial 404 when a dimple 410 and a bump 408 are aligned. Additionally, when a dimple 410 and a bump 408 are not aligned, the bump 408 is compressed against the dimple-less edge of the dial 404 and primed to spring or decompress into a dimple 410 when alignment is achieved.

Figure 7:
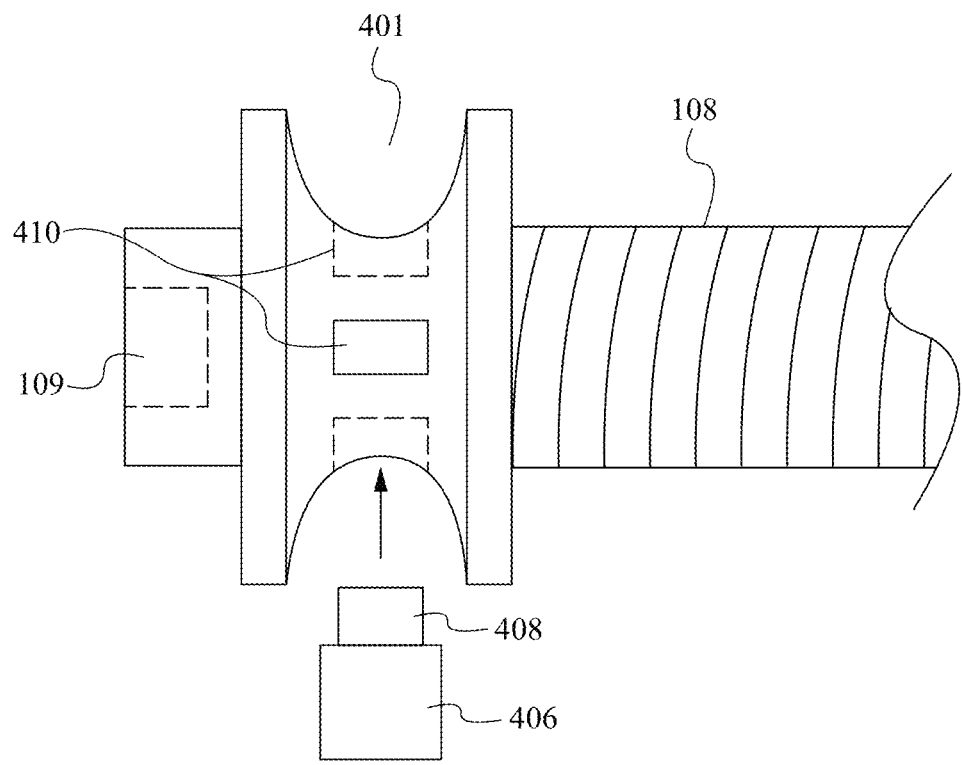
FIG. 7 illustrates a side up-close view of a positioning element and stopper according to some embodiments.

In some embodiments, the dial 404 is held in place within the additional panel apertures 99 by force applied by the bumps 408 of the stoppers 406. For example, in some embodiments the dimples 410 are able to be concave and centered along the perimeter of the dial 404 such that when the bumps 408 are within the dimples 410 the outer walls of the concavity of the dimples 410 prevents the dial 404 and/or the stoppers 406 from falling out of place. As another example, as shown in FIG. 7 the dial 404 is able to be omitted or incorporated into the positioning element 108, wherein the perimeter of the positioning element 108 that is adjacent the stoppers 406 forms a trough or channel 401 that receives the stoppers 406 such that the positioning element 108 is unable to come out of position with respect to the stoppers 406. In such embodiments, the bottom of the trough is able to comprise the dimples 410 for receiving the bumps 408 of the stoppers 406. Alternatively, the dial 404 is able to be otherwise coupled or uncoupled within the apertures 99 by one or more fastening elements as are well known in the art.

In some embodiments, the stoppers 406 are held in place within the additional panel apertures 99 by place holders 407. In particular, the place holders 407 are able to be tensioned and/or compressed by the wall of the apertures 99 when the stoppers 406 are inserted into the apertures 99 and thus provide a spring force against the walls of the apertures 99 to try and relieve that tensioning/compression. Accordingly, the spring force holds the stoppers 406 within the apertures 99. Alternatively, one or more of the stoppers 406 are able to be otherwise coupled or uncoupled within the apertures 99 by one or more fastening elements as are well known in the art. Although as shown in FIG. 4, the device 400 comprises one of the panels 104 including the position locking mechanism 402, wherein the position locking mechanism 402 comprises a single dial 404 having sixteen dimples 410 and two stoppers 406, it is understood that any number of the panels 104 are able to include a position locking mechanism 402 and the position locking mechanism is able to include any number of dials 404 having any number of dimples 410 coupled to any number of stoppers 406. In some embodiments, the additional panel apertures 99 are able to replace the panel aperture 103 and/or the dial aperture 410 is able to be substantially similar to the panel aperture 103 in size and shape.

In operation, as the positioning element 108 is rotated to extend or retract the plates 102, the dial 404 is rotated along with the positioning element 108 and the bumps 408 compress and decompress into and out of the dimples 410 as they move in an out of alignment with the bumps 408. As a result, each point during the rotation of the positioning element 108 that results in an alignment of a bump 408 and a dimple 410 serves as a demarcated degree of rotation and/or degree of extension/retraction of the plates 102. In this way, the position locking mechanism 402 provides the advantage of enabling a user to rotate the positioning element 108 and thereby extend the plates 102 to predetermined rotation/extension amounts and/or by predetermined rotation/extension intervals represented by the spacing and number of dimple 410 and bump 408 alignment points. For example, the position and/or number of dimples 410 and/or bumps 408 of the position locking mechanism 402 is able to be adjusted to adjust the number and/or position of the alignment points and therefore the number and/or position of plate extension points. Thus, the position locking mechanism 402 of the bodiless bone fusion device 400 is able to be tuned to different size devices 400 based on the number of extension increments needed and the desired extension distance interval between each of the increments. In some embodiments, the increments are configured to be constant. Alternatively, the increments are able to be configured to decrease in size as the plates 102 approach the maximum extension level. Alternatively, other increment profiles are able to be used as are well known in the art. Further, the compression of the bumps 408 and their resistance thereto during rotation of the positioning element 108 between alignment points provides a slipping resistance force the resists unintended rotation of the positioning element 108 out of an alignment point. As a result, the position locking mechanism 402 provides the advantage of reducing the chance of the positioning element 108 unintentionally rotating and/or the plates 102 unintentionally extending or retracting.

Figure 5:
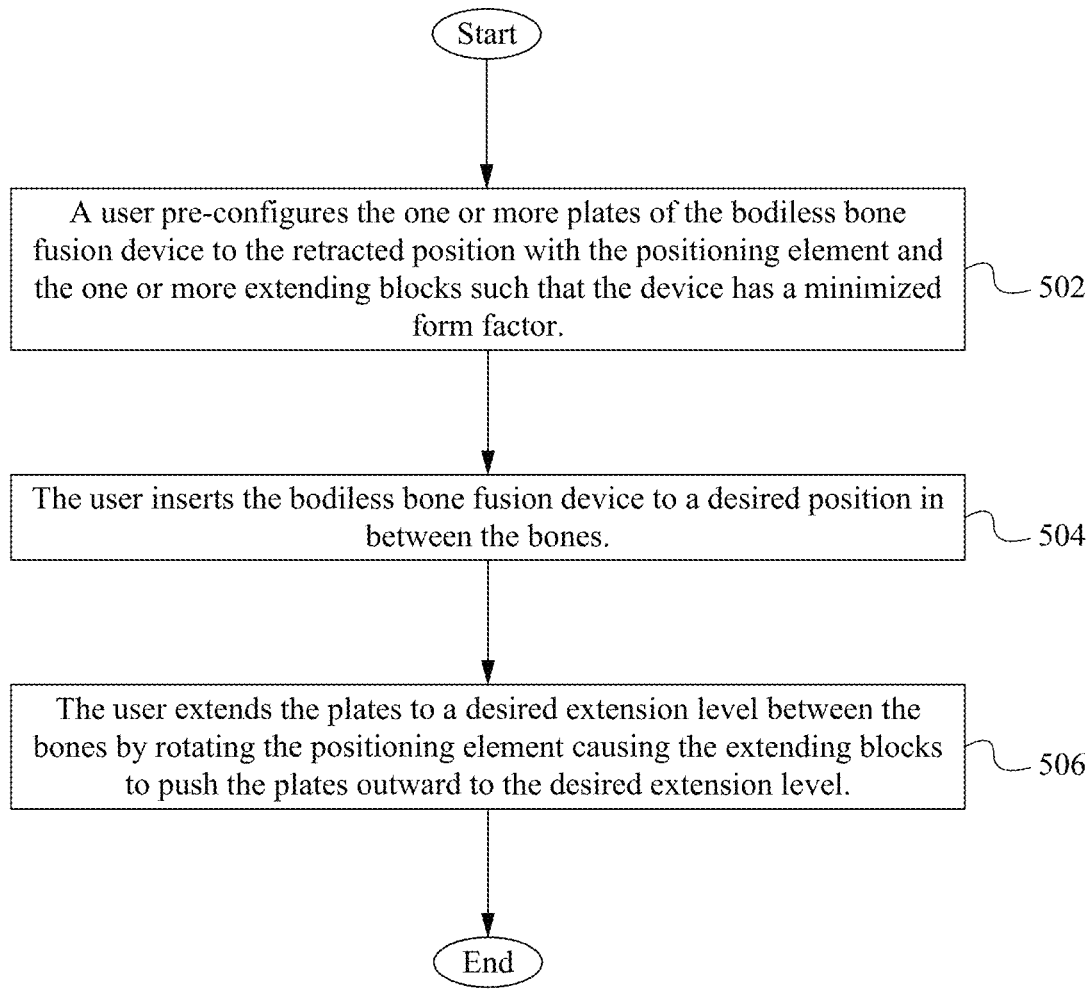
FIG. 5 illustrates a flow chart of a method of using the bodiless bone fusion device according to some embodiments.

FIG. 5 illustrates a flow chart of a method of using a bodiless bone fusion device according to some embodiments. A user pre-configures the one or more plates 102 of the bodiless bone fusion device to the retracted position with the positioning element 108 and the one or more extending blocks 106 such that the device has a minimized form factor at the step 502. The user inserts the bodiless bone fusion device into a desired position in between the bones at the step 504. The user extends the plates 102 to a desired extension level between the bones by rotating the positioning element 108 causing the extending blocks 106 to push the plates 102 outward to the desired extension level at the step 506. In some embodiments, the rotating of the positioning element 108 comprises rotating the positioning element 108 through a number of alignment points of the position locking mechanism 402 until a desired alignment point is reached. As a result, the method is able to provide the benefits of a minimally invasive surgery due to the minimized form factor of the bodiless bone fusion device in the retracted position and a more accurate and stable extension point due to the position locking mechanism.

Figure 9A:
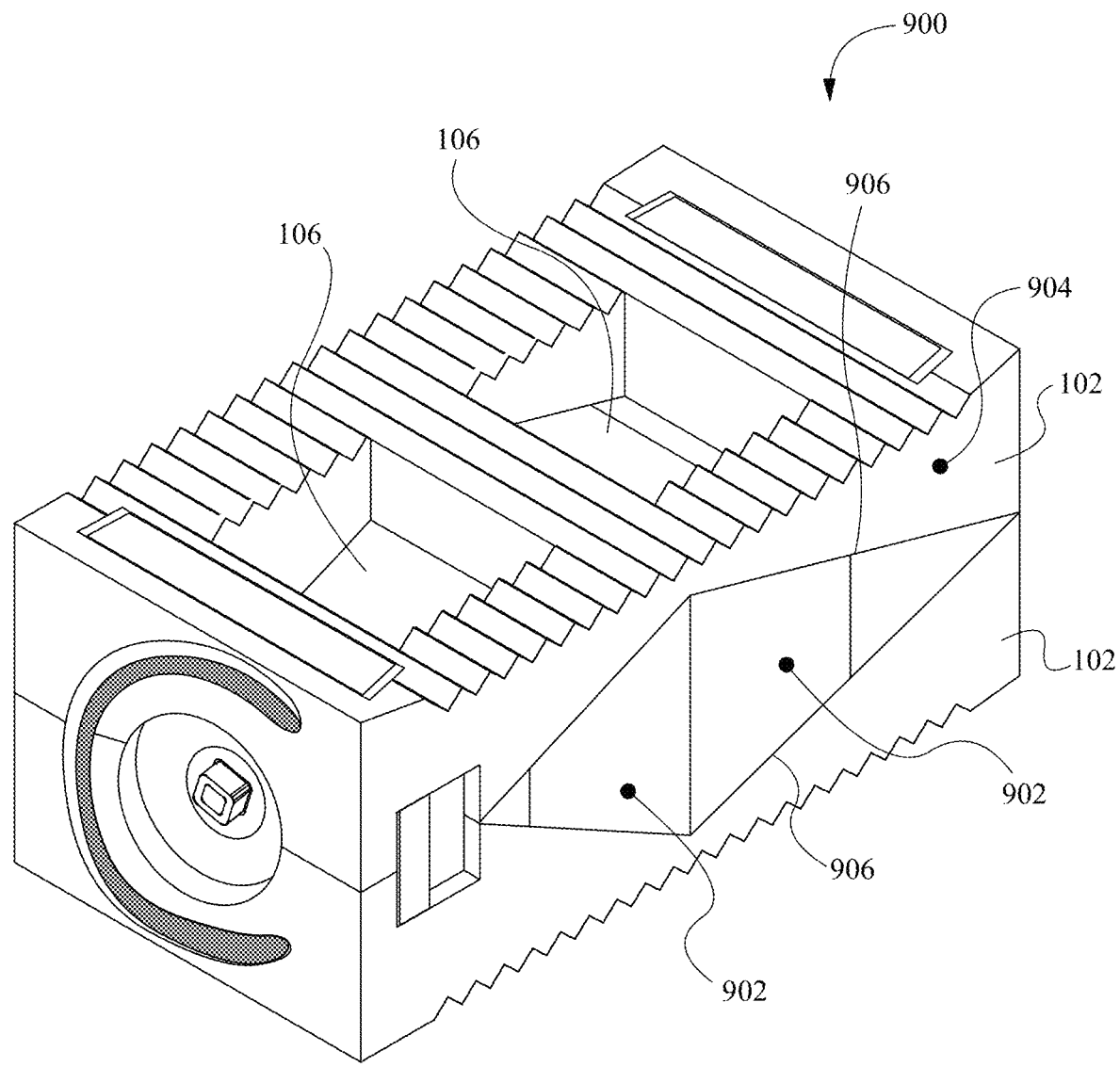
FIG. 9A illustrates a retracted perspective view of a bodiless bone fusion device having stretched extending blocks according to some embodiments.
Figure 9B:
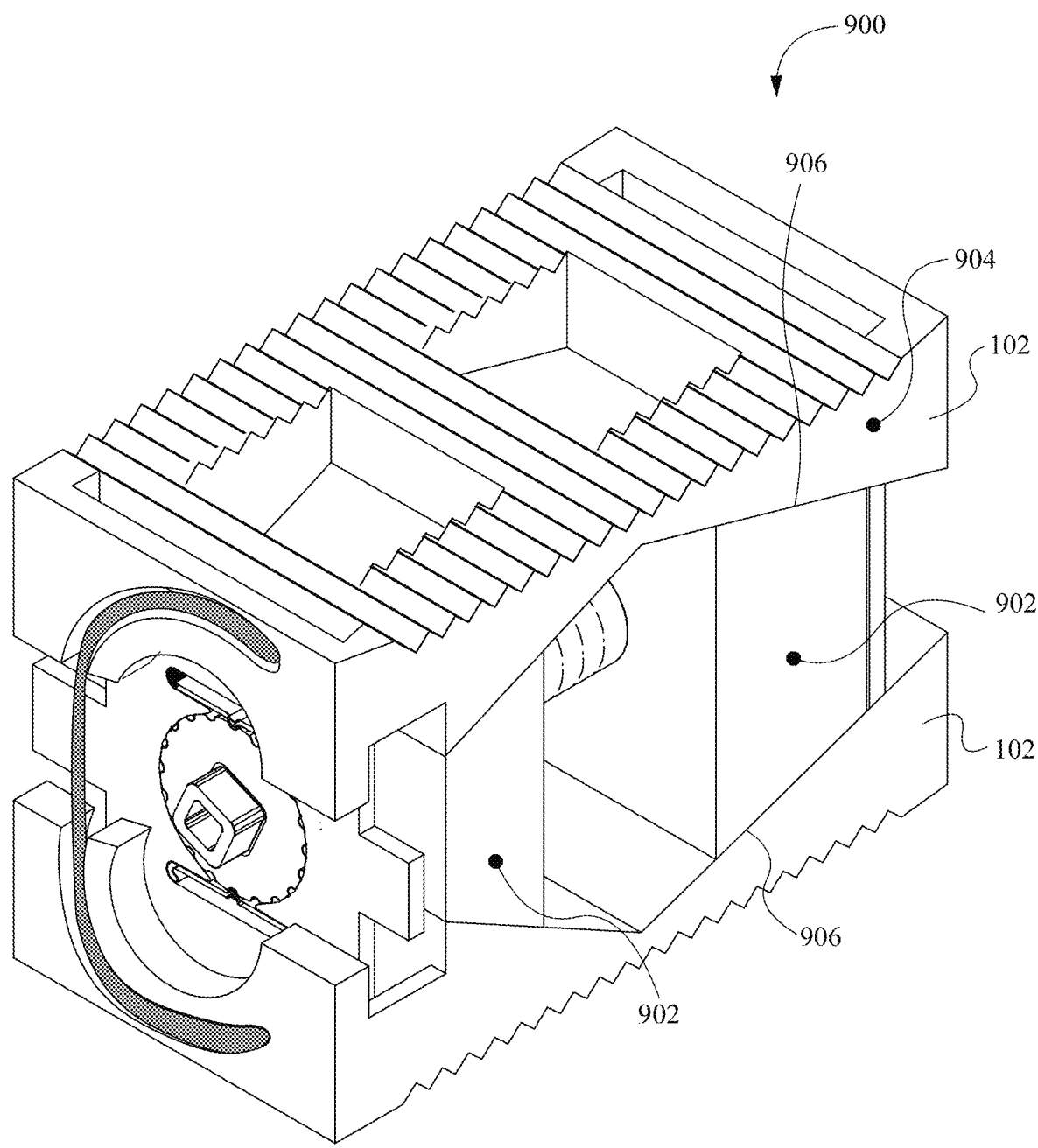
FIG. 9B illustrates an extended perspective view of a bodiless bone fusion device having stretched extending blocks according to some embodiments.

FIGS. 9A and 9B illustrate a retracted perspective view and an extended perspective view of a bodiless bone fusion device 900 having stretched or expanded extending blocks according to some embodiments. The bodiless bone fusion device 900 shown in FIGS. 9A and 9B is substantially similar to the bodiless bone fusion device 100 except for the differences described herein. Specifically, the sides 902 of the extending blocks 106 shown in FIGS. 9A and 9B extend such that the sides 902 substantially align with the outer surface of the device 900. As a result, the extending blocks 106 span the entire width of the plates 102 which creates greater surface area for the blocks 106 to contact the plates 102 as well as greater stability in the extended position as a wider portion of the plates 102 is directly contacted/supported by the blocks 106. In such embodiments, the skirt or sides 904 of the plates 102 are able to comprise a block cavity 906 configured to receive the sides 902 of the blocks 106 when the device 900 is in the retracted position. Although as shown in FIGS. 9A and 9B, both sides 902 of both blocks 106 are expanded to align with the exterior surface of the sides 904 of the plates 102, one or more of the sides 902 of one or more of the blocks 106 are able to not be expanded and/or be expanded less. For example, one of the sides 902 of one of the blocks 106 is able to extend part way into the cavity 906 on one of the sides 904 of the plates 102.

Thus, the bodiless bone fusion device, apparatus and method described herein has numerous advantages. Specifically, the bodiless bone fusion device provides the advantage of maximizing the plate size to device size ratio because the size of the plates is equal to the size of the device in the retracted position creating a 1 to 1 ratio. This enables the device to incorporate larger plates that increase stability and surface area, which would not be possible with devices that incorporate a body. Also, the device provides the advantage of the grip channels that ensure the non-slippage of the driving mechanism during the operation of the bone fusion apparatus. Further, the position locking mechanism provides the advantage of reducing the chance of the positioning element unintentionally rotating and/or the plates unintentionally extending or retracting. Also, as mentioned above, the method of use requires only a small incision and minimally invasive surgical procedure advantageously promoting health and rapid recovery by the patient. Indeed, bone growth occurs around the bodiless bone fusion device and particularly at the locations of the extended plates, such that the bodiless bone fusion device is further secured by the bone growth, which further promotes a superior, robust bone fusion result. Moreover, the device provides the advantage of extending blocks that span the entire width of the plates thereby creating greater surface area for the blocks to contact the plates as well as providing greater stability in the extended position as a wider portion of the plates is directly contacted/supported by the blocks.

The present invention has been described in terms of specific embodiments incorporating details to facilitate the understanding of principles of construction and operation of the invention. Such reference herein to specific embodiments and details thereof is not intended to limit the scope of the claims appended hereto. It will be apparent to those skilled in the art that modification may be made in the embodiments chosen for illustration without departing from the spirit and scope of the invention.

For example, it should be noted that although the above bodiless bone fusion devices are described in reference to a pair of extending blocks, a pair of screws, and wherein each plate is shaped such that the ends are larger than the middle, and the size of the plate gradually increases while going from the middle to the ends, the use of a single extending block in the above embodiments is contemplated. Specifically, if using a single extending block, the above embodiments would operate the same except the positioning element would comprise a single screw that when engaged would cause the single extending block to move from one end of the screw to the other end thereby exerting a force against the plates such that they move into the extended position. In such embodiments, each plate is shaped such that one end is larger than the opposite end, and the size of the plate gradually increases going from the smaller end to the larger end.

What is claimed is:

1. A bone fusion device for insertion into a desired location comprising:
   an extending mechanism including a plurality of extending blocks coupled with a positioning element such that movement of the positioning element causes the plurality of extending blocks to move with respect to the positioning element;
   a first plate; and
   a second plate, the first and second plates coupled with the plurality of extending blocks such that when the plurality of extending blocks move with respect to the positioning element, the first and second plates move along a path with respect to each other between a retracted position in which the first and second plates are adjacent to each other to an extended position in which the first and second plates are spread apart from each other, wherein a portion of the first plate directly contacted by the plurality of extending blocks changes as the plurality of extending blocks move with respect to the positioning element.

2. The device of claim 1, wherein the first and second plates are sized such that an entirety of a perimeter of the first and second plates about the path align with an outermost perimeter of the device about the path.

3. The device of claim 1, further comprising one or more biasing elements physically coupled with both of the first and second plates and positioned such that the one or more biasing elements apply a force resisting the movement of the first and second plates from the retracted position to the extended position.

4. The device of claim 3, wherein the one or more biasing elements have a shape selected from the group consisting of a ring, a C-shape and a ring-shaped coil.

5. The device of claim 1, wherein the plurality of extending blocks each comprise an angled surface between a left side and a right side, wherein the left sides of the plurality of extending blocks are aligned with a left face of the first and second plates and the right sides of the plurality of extending blocks are aligned with a right face of the first and second plates.

6. The device of claim 5, wherein the angled surface forms a continuous sheet between the left and right sides of the plurality extending blocks in order to increase the surface area of the angled surface.

7. The device of claim 1, further comprising a lock coupled with the positioning element and configured to physically bias the rotational orientation of the positioning element into one of a plurality of positions.

8. The device of claim 7, wherein the lock comprises one or more stoppers each having a bump and a dial having one or more dimples and coupled with the positioning element such that the dial rotates with the positioning element, wherein the bumps do not rotate with the dial and the stoppers are positioned adjacent to the dial such that, when aligned, one or more of the bumps spring into one or more of the dimples.

9. The device of claim 8, further comprising one or more support panels coupled with the lock and the extending mechanism, wherein each of the one or more support panels are positioned within a panel aperture on each of the plates such that as the plates move between the retracted and the extended positions the plates slide up or down the panels via the panels apertures.

10. The device of claim 9, wherein at least one of the one or more support panels comprises a pair of grip tabs that protrude from the sides of the support panel into a pair of grip apertures formed by the plates when the plates are in the retracted position.

11. A bone fusion device for insertion into a desired location comprising:
    an extending mechanism including one or more extending blocks coupled with a positioning element such that movement of the positioning element causes the one or more extending blocks to move with respect to the positioning element;
    a first plate;
    a second plate, the first and second plates straddling the extending mechanism and coupled with the one or more extending blocks such that when the one or more extending blocks move with respect to the positioning element, the first and second plates move along a path with respect to each other between a retracted position in which the first and second plates are in contact with each other to an extended position in which the plates are spread apart from and do not contact each other; and
    a lock having a body that contacts the positioning element to physically bias the movement of the positioning element into one of a plurality of positions.

12. The device of claim 11, wherein when in the extended position, the first and second plates are spread apart from and do not directly contact each other.

13. The device of claim 11, further comprising one or more biasing elements coupled with the first plate and the second plate and positioned such that in the extended position the one or more biasing elements extend from the first plate to the second plate, wherein the one or more biasing elements have a shape selected from the group consisting of a ring, a C-shape and a ring-shaped coil.

14. The device of claim 11, wherein the first and second plates are sized such that the entirety of the perimeter of the first and second plates about the path align with the outermost perimeter of the device about the path.

15. The device of claim 11, wherein the bone fusion device further comprises one or more support panels coupled with the extending mechanism, wherein each of the one or more support panels are positioned within a panel aperture on each of the first and second plates such that as the first and second plates move between the retracted and the extended positions the first and second plates slide up or down the panels via the panels apertures.

16. The device of claim 15, wherein at least one of the one or more support panels comprises a pair of grip tabs that protrude from the sides of the support panel into a pair of grip apertures formed by the first and second plates when the first and second plates are in the retracted position.

17. The device of claim 11, wherein the angled surface forms a continuous sheet between the left and right sides of the one or more extending blocks in order to increase the surface area of the angled surface.

18. The device of claim 11, wherein the lock comprises one or more stoppers each having a bump and a dial having one or more dimples and coupled with the positioning element such that the dial rotates with the positioning element, wherein the bumps do not rotate with the dial and the stoppers are positioned adjacent to the dial such that, when aligned, one or more of the bumps spring into one or more of the dimples.

19. The device of claim 18, further comprising one or more support panels coupled with the lock and the extending mechanism, wherein each of the support panels are positioned within a panel aperture on each of the first and second plates such that as the first and second plates move between the retracted and the extended positions the first and second plates slide up or down the panels via the panels apertures.

20. The device of claim 19, wherein at least one of the one or more support panels comprises a pair of grip tabs that protrude from the sides of the support panel into a pair of grip apertures formed by the first and second plates when the first and second plates are in the retracted position.

* * * * *